(12) United States Patent
Petersch et al.

(10) Patent No.: US 12,154,383 B2
(45) Date of Patent: Nov. 26, 2024

(54) METHODS, DEVICES AND SYSTEMS FOR DETERMINING EYE PARAMETERS

(71) Applicant: PUPIL LABS GmbH, Berlin (DE)

(72) Inventors: Bernhard Petersch, Berlin (DE); Kai Dierkes, Berlin (DE)

(73) Assignee: PUPIL LABS GmbH, Berlin (DE)

( * ) Notice: Subject to any disclaimer, the term of this patent is extended or adjusted under 35 U.S.C. 154(b) by 227 days.

(21) Appl. No.: 17/612,628

(22) PCT Filed: May 26, 2020

(86) PCT No.: PCT/EP2020/064593
§ 371 (c)(1),
(2) Date: Nov. 19, 2021

(87) PCT Pub. No.: WO2020/244971
PCT Pub. Date: Dec. 10, 2020

(65) Prior Publication Data
US 2022/0207919 A1 Jun. 30, 2022

(30) Foreign Application Priority Data
May 26, 2020 (WO) .................. PCT/EP2019/064656

(51) Int. Cl.
*G06V 40/18* (2022.01)
*A61B 3/113* (2006.01)
(Continued)

(52) U.S. Cl.
CPC ............ *G06V 40/193* (2022.01); *A61B 3/113* (2013.01); *G02B 27/0093* (2013.01);
(Continued)

(58) Field of Classification Search
None
See application file for complete search history.

(56) References Cited

U.S. PATENT DOCUMENTS

| 4,852,988 A | 8/1989 | Velez et al. |
| 6,091,546 A | 7/2000 | Spitzer |

(Continued)

FOREIGN PATENT DOCUMENTS

| CA | 2967756 | 10/2005 |
| CA | 2750287 | 11/2011 |

(Continued)

OTHER PUBLICATIONS

Notice of Allowance dated Mar. 30, 2022 in U.S. Appl. No. 16/967,304.

(Continued)

*Primary Examiner* — Delomia L Gilliard
(74) *Attorney, Agent, or Firm* — Dicke, Billig & Czaja, PLLC

(57) ABSTRACT

A system and method for generating data suitable for determining one or more parameters of at least one eye of a subject. The method includes receiving image data of an eye at a first time from a camera of known camera intrinsics and defining an image plane. A first ellipse in the image data is determined. The method includes determining a first eye intersecting line in 3D expected to intersect a 3D center of the eyeball at the first time as a line which is, in the direction of the orientation vector, parallel-shifted to the first center line by an expected distance between the center of the eyeball and a center of the pupil.

20 Claims, 4 Drawing Sheets

(51) Int. Cl.
*G02B 27/00* (2006.01)
*G02B 27/01* (2006.01)
*G06F 3/01* (2006.01)
*G06T 7/73* (2017.01)
*G06V 40/19* (2022.01)

(52) U.S. Cl.
CPC ....... *G02B 27/0101* (2013.01); *G02B 27/017* (2013.01); *G06F 3/013* (2013.01); *G06T 7/75* (2017.01); *G06V 40/19* (2022.01); *G06V 40/197* (2022.01); *G02B 2027/0138* (2013.01); *G02B 2027/0178* (2013.01)

(56) References Cited

U.S. PATENT DOCUMENTS

| | | |
|---|---|---|
| 6,351,273 B1 | 2/2002 | Lemelson et al. |
| 6,943,754 B2 | 9/2005 | Aughey et al. |
| 7,488,294 B2 | 2/2009 | Torch |
| 7,815,311 B2 | 10/2010 | Johns et al. |
| 8,342,687 B2 | 1/2013 | Blixt et al. |
| 8,594,374 B1 | 11/2013 | Bozarth |
| 8,624,994 B2 | 1/2014 | Kaneda et al. |
| 8,752,963 B2 | 6/2014 | McCulloch et al. |
| 8,761,459 B2 | 6/2014 | Kaneda et al. |
| 8,830,142 B1 | 9/2014 | Kim et al. |
| 8,836,768 B1 | 9/2014 | Rafii et al. |
| 8,929,589 B2 | 1/2015 | Publicover et al. |
| 8,982,046 B2 | 3/2015 | Edwards et al. |
| 9,185,352 B1 | 11/2015 | Jacques |
| 9,189,095 B2 | 11/2015 | Eden et al. |
| 9,207,760 B1 | 12/2015 | Wu et al. |
| 9,253,442 B1 | 2/2016 | Pauli |
| 9,380,287 B2 | 6/2016 | Nistico et al. |
| 9,405,365 B2 | 8/2016 | Publicover et al. |
| 9,451,166 B1 | 9/2016 | Ribardo, Jr. et al. |
| 9,501,683 B1 | 11/2016 | Hatstat et al. |
| 9,529,442 B2 | 12/2016 | Cho et al. |
| 9,600,069 B2 | 3/2017 | Publicover et al. |
| 9,668,648 B2 | 6/2017 | Pfleger et al. |
| 9,672,416 B2 | 6/2017 | Zhang et al. |
| 9,693,684 B2 | 7/2017 | Lopez et al. |
| 9,727,136 B2 | 8/2017 | Willairat et al. |
| 9,737,209 B2 | 8/2017 | Gramatikov et al. |
| 9,785,233 B2 | 10/2017 | San Agustin Lopez et al. |
| 9,801,539 B2 | 10/2017 | Kerr et al. |
| 9,811,158 B2 | 11/2017 | Hennessey et al. |
| 9,851,091 B2 | 12/2017 | Im et al. |
| 9,936,195 B2 | 4/2018 | Horesh |
| 9,958,941 B2 | 5/2018 | Gustafsson et al. |
| 9,961,307 B1 | 5/2018 | Weinblatt |
| 9,977,960 B2 | 5/2018 | Gustafsson et al. |
| 10,016,131 B2 | 7/2018 | Liu et al. |
| 10,048,749 B2 | 8/2018 | Miao et al. |
| 10,114,459 B2 | 10/2018 | Algotsson et al. |
| 10,157,313 B1 | 12/2018 | Zhang et al. |
| 10,229,511 B2 | 3/2019 | Meier |
| 10,285,589 B2 | 5/2019 | Hart et al. |
| 10,303,250 B2 | 5/2019 | Jeong |
| 10,307,053 B2 | 6/2019 | Fayolle |
| 10,416,764 B2 | 9/2019 | Wanner et al. |
| 10,438,373 B2 | 10/2019 | Wang et al. |
| 10,452,137 B2 | 10/2019 | Noda et al. |
| 10,488,668 B2 | 11/2019 | Cazalet |
| 10,489,680 B2 | 11/2019 | Aliabadi et al. |
| 10,496,160 B2 | 12/2019 | Lu et al. |
| 10,514,542 B2 | 12/2019 | Erinjippurath et al. |
| 10,546,193 B2 | 1/2020 | Schmidt et al. |
| 10,546,194 B2 | 1/2020 | Tsurumi |
| 10,634,934 B2 | 4/2020 | Chene et al. |
| 10,698,205 B2 | 6/2020 | Huang |
| 10,909,711 B2 | 2/2021 | Schroeder et al. |
| 10,976,813 B2 | 4/2021 | Nistico et al. |
| 11,017,558 B2 | 5/2021 | Noble et al. |
| 11,023,038 B2 | 6/2021 | Yasuda et al. |
| 11,033,204 B2 | 6/2021 | Massonneau et al. |
| 2003/0184868 A1 | 10/2003 | Geist |
| 2004/0174496 A1 | 9/2004 | Ji et al. |
| 2005/0034287 A1 | 2/2005 | Xie |
| 2005/0225723 A1 | 10/2005 | Pilu |
| 2006/0240005 A1 | 10/2006 | Velardi |
| 2006/0279692 A1 | 12/2006 | Bruck |
| 2007/0066916 A1 | 3/2007 | Lemos |
| 2009/0190026 A1 | 7/2009 | Chen |
| 2010/0045933 A1 | 2/2010 | Eberl et al. |
| 2010/0053555 A1 | 3/2010 | Enriquez et al. |
| 2010/0220288 A1 | 9/2010 | Cleveland |
| 2012/0212593 A1 | 8/2012 | Na'aman et al. |
| 2012/0290401 A1 | 11/2012 | Neven |
| 2012/0293773 A1 | 11/2012 | Publicover et al. |
| 2013/0050070 A1 | 2/2013 | Lewis et al. |
| 2013/0066213 A1 | 3/2013 | Wellington |
| 2013/0069883 A1 | 3/2013 | Oga |
| 2013/0083976 A1* | 4/2013 | Ragland ............... A61B 3/113 382/117 |
| 2013/0100025 A1 | 4/2013 | Vernacchia |
| 2013/0114043 A1 | 5/2013 | Balan et al. |
| 2013/0120224 A1 | 5/2013 | Cajigas et al. |
| 2013/0207887 A1 | 8/2013 | Raffle et al. |
| 2013/0222213 A1 | 8/2013 | Abdollahi et al. |
| 2013/0318776 A1 | 12/2013 | Jacobs et al. |
| 2013/0321925 A1 | 12/2013 | Jacobs et al. |
| 2014/0022371 A1 | 1/2014 | Huang et al. |
| 2014/0043581 A1 | 2/2014 | Chen |
| 2014/0049452 A1 | 2/2014 | Maltz |
| 2014/0055591 A1 | 2/2014 | Katz |
| 2014/0055746 A1 | 2/2014 | Nistico et al. |
| 2014/0055747 A1 | 2/2014 | Nistico et al. |
| 2014/0152558 A1 | 6/2014 | Salter et al. |
| 2014/0156219 A1 | 6/2014 | Soubra et al. |
| 2014/0191927 A1 | 7/2014 | Cho |
| 2014/0218281 A1 | 8/2014 | Amayeh et al. |
| 2014/0226131 A1 | 8/2014 | Lopez et al. |
| 2014/0247232 A1 | 9/2014 | George-Svahn et al. |
| 2014/0285404 A1 | 9/2014 | Takano et al. |
| 2014/0354953 A1 | 12/2014 | Chen et al. |
| 2015/0070470 A1 | 3/2015 | McMurrough |
| 2015/0085251 A1 | 3/2015 | Larsen |
| 2015/0169050 A1 | 6/2015 | Publicover et al. |
| 2015/0181100 A1 | 6/2015 | Publicover et al. |
| 2015/0302585 A1 | 10/2015 | VanBlon et al. |
| 2015/0310263 A1 | 10/2015 | Zhang et al. |
| 2016/0004306 A1 | 1/2016 | Maltz |
| 2016/0005176 A1 | 1/2016 | Nguyen et al. |
| 2016/0011658 A1 | 1/2016 | Lopez et al. |
| 2016/0166190 A1 | 1/2016 | Publicover et al. |
| 2016/0109945 A1 | 4/2016 | Kempinski |
| 2016/0126675 A2 | 5/2016 | Daoura |
| 2016/0166146 A1 | 6/2016 | Sarkar |
| 2016/0187969 A1 | 6/2016 | Larsen et al. |
| 2016/0202756 A1 | 7/2016 | Wu et al. |
| 2016/0206196 A1 | 7/2016 | Pfleger et al. |
| 2016/0224110 A1 | 8/2016 | Massonneau et al. |
| 2016/0246367 A1 | 8/2016 | Tungare et al. |
| 2016/0252751 A1 | 9/2016 | Kim |
| 2016/0262608 A1 | 9/2016 | Krueger |
| 2016/0267708 A1 | 9/2016 | Nistico et al. |
| 2016/0286110 A1 | 9/2016 | Ribardo, Jr. et al. |
| 2016/0328016 A1 | 11/2016 | Andersson et al. |
| 2017/0004363 A1 | 1/2017 | Dore et al. |
| 2017/0017299 A1 | 1/2017 | Biedert et al. |
| 2017/0031437 A1 | 2/2017 | Qian et al. |
| 2017/0035293 A1 | 2/2017 | Nistico et al. |
| 2017/0038607 A1 | 2/2017 | Camara |
| 2017/0116476 A1 | 4/2017 | Publicover et al. |
| 2017/0123491 A1 | 5/2017 | Hansen |
| 2017/0136626 A1 | 5/2017 | Wang et al. |
| 2017/0176778 A1 | 6/2017 | Ushakov |
| 2017/0188823 A1 | 7/2017 | Ganesan et al. |
| 2017/0243387 A1 | 8/2017 | Li et al. |
| 2017/0276934 A1 | 9/2017 | Sarkar |
| 2017/0308734 A1 | 10/2017 | Chalom et al. |
| 2017/0332901 A1 | 11/2017 | Hwang et al. |
| 2017/0351326 A1 | 12/2017 | Aarts et al. |

(56) References Cited

U.S. PATENT DOCUMENTS

| | | | |
|---|---|---|---|
| 2017/0363885 A1 | 12/2017 | Blum et al. | |
| 2017/0372487 A1 | 12/2017 | Lagun et al. | |
| 2018/0018451 A1 | 1/2018 | Spizhevoy et al. | |
| 2018/0032131 A1 | 2/2018 | Yasuda et al. | |
| 2018/0059782 A1 | 3/2018 | San Agustin et al. | |
| 2018/0089834 A1 | 3/2018 | Spizhevoy et al. | |
| 2018/0095295 A1* | 4/2018 | Chene | A61B 3/107 |
| 2018/0103194 A1 | 4/2018 | Tang | |
| 2018/0103903 A1 | 4/2018 | Tzvieli et al. | |
| 2018/0137358 A1 | 5/2018 | Rousseau et al. | |
| 2018/0157045 A1 | 6/2018 | Davami | |
| 2018/0157892 A1 | 6/2018 | Han et al. | |
| 2018/0180893 A1 | 6/2018 | Gupta | |
| 2018/0181809 A1 | 6/2018 | Ranjan et al. | |
| 2018/0267604 A1 | 9/2018 | Bhattacharya | |
| 2018/0286070 A1 | 10/2018 | Benedetto | |
| 2019/0005679 A1 | 1/2019 | Nie | |
| 2019/0043216 A1 | 2/2019 | Yabuuchi et al. | |
| 2019/0076015 A1 | 3/2019 | Johansson et al. | |
| 2019/0080474 A1 | 3/2019 | Lagun et al. | |
| 2019/0082170 A1 | 3/2019 | Akahori | |
| 2019/0086669 A1 | 3/2019 | Percival et al. | |
| 2019/0087973 A1 | 3/2019 | Kaehler et al. | |
| 2019/0156100 A1 | 5/2019 | Rougeaux et al. | |
| 2019/0265788 A1 | 8/2019 | Yosha et al. | |
| 2020/0183190 A1 | 6/2020 | Rousseau et al. | |
| 2020/0335065 A1 | 10/2020 | Furuta et al. | |
| 2020/0364453 A1 | 11/2020 | Tonsen et al. | |
| 2021/0041701 A1 | 2/2021 | Kassner et al. | |
| 2021/0049410 A1 | 2/2021 | Dierkes et al. | |
| 2021/0247617 A1 | 8/2021 | Kassner et al. | |

FOREIGN PATENT DOCUMENTS

| | | |
|---|---|---|
| CN | 102930252 | 2/2013 |
| CN | 103356163 | 10/2013 |
| CN | 105676456 | 6/2016 |
| CN | 106599994 | 4/2017 |
| CN | 206805020 | 12/2017 |
| CN | 107545302 | 1/2018 |
| CN | 107564062 | 1/2018 |
| CN | 109254420 | 1/2019 |
| CN | 109298533 | 2/2019 |
| CN | 109820524 | 5/2019 |
| DE | 19807902 | 9/1999 |
| DE | 102009049849 | 4/2011 |
| DE | 10 2010 018 562 | 10/2011 |
| DE | 10 2014 206 623 | 10/2015 |
| DE | 10 2016 210 288 | 12/2017 |
| EP | 1403680 | 3/2004 |
| EP | 1755441 | 2/2007 |
| EP | 1027627 | 2/2009 |
| EP | 2096577 | 9/2009 |
| EP | 2309307 | 4/2011 |
| EP | 2416280 | 2/2012 |
| EP | 2490155 | 8/2012 |
| EP | 2573650 | 3/2013 |
| EP | 2784632 | 10/2014 |
| EP | 2805671 | 11/2014 |
| EP | 2886041 | 6/2015 |
| EP | 2795888 | 9/2015 |
| EP | 2940555 | 11/2015 |
| EP | 2943835 | 11/2015 |
| EP | 2956844 | 12/2015 |
| EP | 2980628 | 2/2016 |
| EP | 3005030 | 4/2016 |
| EP | 3047883 | 7/2016 |
| EP | 3059629 | 8/2016 |
| EP | 3112922 | 1/2017 |
| EP | 3129849 | 2/2017 |
| EP | 3135464 | 3/2017 |
| EP | 3137938 | 3/2017 |
| EP | 3228238 | 10/2017 |
| EP | 3236338 | 10/2017 |
| EP | 3252566 | 12/2017 |
| EP | 3258308 | 12/2017 |
| EP | 3267295 | 2/2018 |
| EP | 3305176 | 4/2018 |
| EP | 3305179 | 4/2018 |
| EP | 3376163 | 9/2018 |
| EP | 3460785 | 3/2019 |
| EP | 3521911 | 8/2019 |
| FR | 3081565 | 11/2019 |
| TW | M401786 | 4/2011 |
| WO | 9905988 | 2/1999 |
| WO | 9926126 | 5/1999 |
| WO | 2005009466 | 2/2005 |
| WO | 2005094667 | 10/2005 |
| WO | 2007/016739 | 2/2007 |
| WO | 2009043927 | 4/2009 |
| WO | 2010071928 | 7/2010 |
| WO | 2011/144932 | 11/2011 |
| WO | 2012052061 | 4/2012 |
| WO | 2013059940 | 5/2013 |
| WO | 2013067230 | 5/2013 |
| WO | 2014/033306 | 3/2014 |
| WO | 2014085789 | 6/2014 |
| WO | 2014186620 | 11/2014 |
| WO | 2015024031 | 2/2015 |
| WO | 2015/051834 | 4/2015 |
| WO | 2015/072202 | 5/2015 |
| WO | 2015/179253 | 11/2015 |
| WO | 2016025583 | 2/2016 |
| WO | 2016074861 | 5/2016 |
| WO | 2016078911 | 5/2016 |
| WO | 2016097919 | 6/2016 |
| WO | 2016111880 | 7/2016 |
| WO | 2016146486 | 9/2016 |
| WO | 2016146488 | 9/2016 |
| WO | 2017001146 | 1/2017 |
| WO | 2017025486 | 2/2017 |
| WO | 2017027352 | 2/2017 |
| WO | 2017/046419 | 3/2017 |
| WO | 2017053966 | 3/2017 |
| WO | 2017053971 | 3/2017 |
| WO | 2017053972 | 3/2017 |
| WO | 2017053974 | 3/2017 |
| WO | 2017/096396 | 6/2017 |
| WO | 2017151206 | 9/2017 |
| WO | 2017/216118 | 12/2017 |
| WO | 2018000020 | 1/2018 |
| WO | 2018000039 | 1/2018 |
| WO | 2018063451 | 4/2018 |
| WO | 2018149875 | 8/2018 |

OTHER PUBLICATIONS

Swirski, Dodgson: "A fully-automatic, temporal approach to single camera, glint-free 3D eye model fitting", Proc. PETMEI Lund/Sweden, Aug. 13, 2013.

Safaee-Rad, R., Tchoukanov, I., Smith, K., & Benhabib, B. (1992). "Three-dimensional location estimation of circular features for machine vision", IEEE Transactions on Robotics and Automation, 8(5), 624-640.

Dierkes, Kassner, Bulling: "A novel approach to single camera, glint-free 3D eye model fitting including corneal refraction", Proc. ETRA Warsaw/Poland Jun. 2018.

Dierkes, Kassner, Bulling: "A fast approach to refraction-aware eye-model fitting and gaze prediction", Proc. ETRA Denver/USA Jun. 25-28, 2019.

Non-Final Office Action dated Apr. 14, 2021 in U.S. Appl. No. 16/967,090. (126).

Notice of Allowance dated Jul. 21, 2021 in U.S. Appl. No. 16/967,090. (126).

Notice of Allowance dated Oct. 20, 2021 in U.S. Appl. No. 16/967,090. (126).

Non-Final Office Action dated Dec. 17, 2021 in U.S. Appl. No. 16/967,304. (127).

Non-Final Office Action dated Jun. 23, 2021 in U.S. Appl. No. 16/967,323 (128).

Final Office Action dated Nov. 5, 2021 in U.S. Appl. No. 16/967,323 (128).

(56) References Cited

OTHER PUBLICATIONS

Non-Final Office Action dated Jan. 27, 2022 in U.S. Appl. No. 16/967,323 (128).
Non-Final Office Action dated Jun. 24, 2021 in U.S. Appl. No. 16/967,363 (129).
Final Office Action dated Jan. 6, 2022 in U.S. Appl. No. 16/967,363 (129).
Krafka, Building Real-Time Unconstrained, Eye Tracking with Deep Learning, B.S., University of Georgia, Dec. 2015. (112 pgs.).
Krafka, et al., "Eye Tracking for Everyone", University of Georgia, pp. 2176-2184, 2016. (9 pgs.).
Abstract Book—CVPR—2016 Main Conference and Workshops, 2016.
Moritz Kassner, Will Patera, Andreas Bulling: "Pupil: An Open Source Platform for Pervasive Eye Tracking and Mobile Gaze-based Interaction", Proceedings of the 2014 ACM International Joint Conference on Pervasive and Ubiquitous Computing: Adjunct Publication, pp. 1151-1160, ACM Sep. 13-17, 2014.
Marc Tonsen, Andreas Bulling et al: "InvisibleEye: Mobile Eye Tracking Using Multiple Low-Resolution Cameras and Learning-Based Gaze Estimation", Proceedings of the ACM on Interactive, Mobile, Wearable and Ubiquitous Technologies, vol. 1, No. 3, Article 106, Sep. 2017.
Mayberry, Addison, et al. "iShadow: design of a wearable, real-time mobile gaze tracker." Proceedings of the 12th annual international conference on Mobile systems, applications, and services, p. 82-94, ACM, 2014.
Mayberry PhD thesis, Leveraging Eye Structure and Motion to Build a Low-Power Wearable Gaze Tracking System, Oct. 2018.
Ishiguro, Yoshio, et al. "Aided eyes: eye activity sensing for daily life." Proceedings of the 1st Augmented Human International Conference. ACM, 2010.
Fuhl, Wolfgang, et al. "PupilNet: convolutional neural networks for robust pupil detection." arXiv preprint arXiv:1601.04902 (2016).
Baluja, Shumeet, and Dean Pomerleau. "Non-intrusive gaze tracking using artificial neural networks." Advances in Neural Information Processing Systems. 1994.
Pomplun et al. "An artificial neural network for high precision eye movement tracking", Advances in Artificial Intelligence, vol. 861 of the series Lecture Notes in Computer Science, pp. 63-69. 2005.

Zhang, Xucong, et al. "Appearance-based gaze estimation in the wild." Proceedings of the IEEE Conference on Computer Vision and Pattern Recognition. 2015.
Zhang, Xucong, et al. "It's written all over your face: Full-face appearance-based gaze estimation." Computer Vision and Pattern Recognition Workshops (CVPRW), 2017 IEEE Conference on. IEEE, 2017.
Feng Lu, Yusuke Sugano, Takahiro Okabe, and Yoichi Sato: "Adaptive Linear Regression for Appearance-Based Gaze Estimation", IEEE transactions on pattern analysis and machine intelligence (TPAMI) 36, 10 (2014), 2033-2046.
Cihan Topal, Serkan Gunal, Onur Koçdeviren, Atakan Doğan, and Ömer N Gerek: "A Low-Computational Approach on Gaze Estimation With Eye Touch System", IEEE transactions on Cybernetics 44, 2 (2013), 228-239.
Krafka, et al. "Eye tracking for everyone." IEEE Conference on Computer Vision and Pattern Recognition (CVPR), pp. 2176-2184, 2016.
Sugano, Bulling: "Self-calibrating head-mounted eye trackers using egocentric visual saliency." In Proc. ACM Symposium on User Interface Software and Technology (UIST 2015). 363-372.
Huang, Veeraraghavan, Sabharwal: "TabletGaze: Unconstrained appearance-based gaze estimation in mobile tablets"Jul. 16, 2016.
Hickson et al., "Eyemotion: Classifying facial expressions in VR using eye-tracking cameras", arXiv:1707.07204v2 [cs.CV] Jul. 28, 2017.
Anjith George, Aurobinda Routray: "Real-time Eye Gaze Direction Classification Using Convolutional Neural Network", IEEE InternationalConference on Signal Processing and Communication, SPCOM 2016.
Olszewski, K., Lim, J., Saito, S., Li, H.: "High-Fidelity Facial and Speech Animation for VR HMDs". ACM Trans. Graph.35, 6, Article 221 (Nov. 2016).
"Pogocam", Youtube, Jan. 6, 2017, URL: https://www.youtube.com/watc67v=pHumrhISYx4.
Santini, Fuhl, Kasneci: "CalibMe: Fast and Unsupervised Eye Tracker Calibration for Gaze-Based Pervasive Human-Computer Interaction", Proc. CHI 2017, May 6-11, 2017.
Bace, Staal, Sörös: "Wearable Eye Tracker Calibration at Your Fingertips", Proc. ETRA 2018, Jun. 14-17, 2018, Warsaw/Poland.

* cited by examiner

METHODS, DEVICES AND SYSTEMS FOR DETERMINING EYE PARAMETERS

CROSS-REFERENCE TO RELATED APPLICATIONS

This Utility Patent Application claims priority under 35 U.S.C. § 371 to International Application Serial No. PCT/EP2020/064593, filed May 26, 2020, which claims priority to International Application Serial No. PCT/EP2019/064656, filed Jun. 5, 2019, which are both incorporated herein by reference in its entirety.

TECHNICAL FIELD

Embodiments of the present invention relate to methods, devices and systems that may be used in the context of eye tracking, in particular a method for generating data suitable for determining a parameter of an eye of a human or animal subject, such as one or more gaze- or eye-related parameters, like eyeball positions, gaze directions or pupil size.

BACKGROUND

Over the last decades, camera-based eye trackers have become a potent and wide-spread research tool in many fields including human-computer interaction, psychology, and market research. Offering increased mobility compared to remote eye-tracking solutions, head-mounted eye trackers, in particular, have enabled the acquisition of gaze data during dynamic activities also in outdoor environments. Many eye trackers rely on complex optical setups involving the active generation of corneal reflections (so called "glints") by means of infrared (IR) LEDs and/or pairs of calibrated stereo cameras. Glint-based (i.e. using corneal reflections) gaze estimation needs to reliably detect those reflections in the camera image and needs to be able to associate each with a unique light source. If successful, the 3D position of the cornea center (assuming a known radius of curvature, i.e. some kind of 3D eye model) can be determined. Beside hardware requirements, one issue encountered in this approach are spurious reflections produced by other illuminators, which may strongly impact the achievable accuracy. From an engineering point of view, glint-free estimation of gaze-related and other parameters of an eye is therefor highly desirable. However, determining of eye parameters from camera images alone (solving an inverse problem) is challenging and so far requires comparatively high computing power often limiting the application area, in particular if head and/or eye movement with respect to the camera is to be compensated (e.g. "slippage" of a head-mounted eye tracker). Head-mounted eye trackers are in general desired to resolve ambiguities during parameter estimation with more restricted hardware setups than remote eye-trackers.

In an alternative to "glint-based" methods for eye parameter estimation, methods which instead derive a 3D eye model location and gaze direction directly from the pupil shape, without the use of any artificially produced reflections exist. One of the challenges of such methods is the size-distance ambiguity: given only one 2D image of an eye it is not possible to know a priori whether the pupil of the eye is small and close or large and far away. Resolving this ambiguity usually requires a time series of many camera images which show the eye under largely varying gaze angles with respect to the camera, and complex numerical methods to optimize the 3D eye model in an iterative fashion to yield the final eyeball center coordinates in camera coordinate space, which in turn are needed to derive quantities like the 3D gaze vector or the pupil size in physical units, such as millimeters.

Pupillometry—the study of temporal changes in pupil diameter as a function of external light stimuli or cognitive processing—is another field of application of general purpose eye-trackers and requires accurate measurements of pupil dilation. Average human pupil diameters are of the order of 3 mm (size of the aperture stop), while peak dilation in cognitive processes can amount to merely a few percent with respect to a baseline pupil size, thus demanding for sub-millimetre accuracy. Video-based eye trackers are in general able to provide apparent (entrance) pupil size signals. However, the latter are usually subject to pupil foreshortening errors—the combined effect of the change of apparent pupil size as the eye rotates away from or towards the camera and the gaze-angle dependent influence of corneal refraction. Also, many prior art methods and devices only provide pupil size in (pixel-based) arbitrary units, while there is an inherent merit in providing an absolute value in units of physical length (e.g. [mm]), since cognitively induced absolute changes are largely independent of baseline pupil radius, and hence only measuring absolute values makes experiments comparable.

Accordingly, there is a need to further improve the speed, robustness and accuracy of the detection of gaze direction, pupil size and other parameters of an eye and reduce the computational effort required therefor.

SUMMARY

According to an embodiment of a method for generating data suitable for determining one or more parameters of at least one eye of a subject, the eye comprising an eyeball and an iris defining a pupil, the method includes receiving image data of an eye at a first time from a camera of known camera intrinsics and defining an image plane, determining a first ellipse in the image data, the first ellipse at least substantially representing a border of the pupil at the first time, using the camera intrinsics and the first ellipse to determine a 3D orientation vector of a first circle in 3D and a first center line on which a center of the first circle is located in 3D, so that a projection of the first circle, in a direction parallel to the first center line, onto the image plane is expected to reproduce the first ellipse, and determining a first eye intersecting line in 3D expected to intersect a 3D center of the eyeball at the first time as a line which is, in the direction of the orientation vector, parallel-shifted to the first center line by an expected distance between the center of the eyeball and a center of the pupil.

According to an embodiment of a system, the system comprises a device and a computing and control unit, the device comprises at least one camera of known camera intrinsics for producing image data including at least one eye of a subject, and the computing and control unit is configured to execute steps of methods for generating data suitable for determining one or more parameters of the at least one eye of the subject, in particular methods as explained herein.

Other embodiments include (non-volatile) computer-readable storage media or devices, and one or more computer programs recorded on one or more computer-readable storage media or computer storage devices. Computer programs can be configured to perform particular operations or processes by virtue of including instructions that, when executed by one or more processors of a system, in particular a system comprising the devices as explained herein, cause the system to perform the operations or processes.

BRIEF DESCRIPTION OF THE DRAWINGS

The components in the figures are not necessarily to scale, instead emphasis being placed upon illustrating the principles of the invention. Moreover, in the figures, like reference numerals designate corresponding parts. In the drawings.

DETAILED DESCRIPTION

Figure 1A:
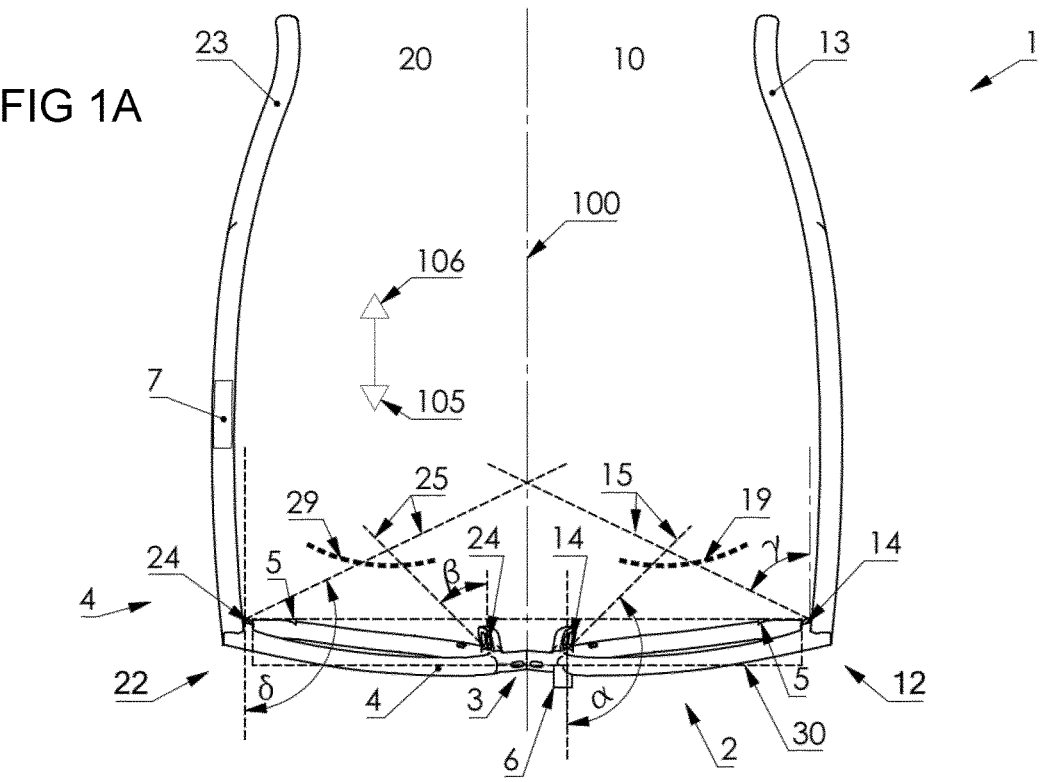
FIGS. 1A-1C illustrate a top, front and lateral views of a device according to an embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

The terms "user" and "subject" are used interchangeably and designate a human or animal being having one or more eyes.

The term "3D" is used to signify "three-dimensional".

It is a task of the invention to provide methods, systems and devices allowing for improved generating, in particular computationally faster, easier and/or more reliably generating of data suitable for determining parameters of a human or animal eye using a device including one or more cameras for generating image data of one or more respective eyes of a subject or user within the field-of-view of the device.

Said task is solved by the subject matter of the independent claims.

The device may be a head-wearable device, configured for being wearable on a user's head and may be used for determining one or more gaze- and/or eye-related parameters of a user wearing the head-wearable device.

Alternatively, the device may be remote from the subject, such as a commonly known remote eye-tracking camera module.

The head-wearable device may be implemented as (head-wearable) spectacles device comprising a spectacles body, which is configured such that it can be worn on a head of a user, for example in a way usual glasses are worn. Hence, the spectacles device when worn by a user may in particular be supported at least partially by a nose area of the user's face. The head-wearable device may also be implemented as an augmented reality (AR-) and/or virtual reality (VR-) device (AR/VR headset), in particular a goggles, or a head-mounted display (HMD). For the sake of clarity, devices are mainly described with regard to head-wearable spectacles devices in the following.

The state of usage of the head-wearable (spectacles) device being arranged at the user's face will be further defined as the "intended use" of the spectacles device, wherein direction and position references, for example horizontal and vertical, parallel and perpendicular, left and right, front and back, up and down, etc., refer to this intended use. As a consequence, lateral positions as left and right, an upper and lower position, and a front/forward and back/backward are to be understood from user's usual view. Equally, this applies to a horizontal and vertical orientation, wherein the user's head during the intended use is in a normal, hence upright, non-tilted, non-declined and non-nodded position.

The spectacles body (main body) typically includes a left ocular opening and a right ocular opening, which mainly come with the functionality of allowing the user to look through these ocular openings. The spectacles body may, at least partially or completely, form the ocular openings by delimiting these from the surrounding. In this case, the spectacles body functions as a frame for the optical openings. Said frame is not necessarily required to form a complete and closed surrounding of the ocular openings.

In addition, a middle plane of the spectacles body may be identified. In particular, said middle plane describes a structural centre plane of the spectacles body, wherein respective structural components or portions, which are comparable or similar to each other, are placed on each side of the middle plane in a similar manner.

Further, the spectacles body typically includes a nose bridge portion, a left lateral portion and a right lateral portion, wherein the middle plane intersects the nose bridge portion, and the respective ocular opening is located between the nose bridge portion and the respective lateral portion.

Typically, a frame of the spectacles body is essentially symmetrical to the middle plane, wherein only minor areas, portions or elements of the frame are non-symmetrical.

The device has at least one camera having a sensor arranged in or defining an image plane for producing image data, typically taking images, of one or more eyes of the user, e.g. of a left and/or a right eye of the user. In other words, the camera, which is in the following also referred to as eye camera, may be a single camera of the device. This may in particular be the case if the device is remote from the user. As used herein, the term "remote" shall describe distances of approximately more than 20 centimeters from the eye(s) of the user. In such a setup, a single eye camera may be able to produce image data of more than one eye of the user simultaneously, in particular images which show both a left and right eye of a user.

Alternatively, the device may have more than one eye camera. This may in particular be the case if the device is a head-wearable device. Such devices are located in close proximity to the user when in use. An eye camera located on such a device may thus only be able to view and image one eye of the user. Such a camera is often referred to as near-eye camera. Typically, head-wearable devices thus comprise more than one (near-)eye camera, for example, in a binocular setup, at least a first or left (side) eye camera and a second or right (side) eye camera, wherein the left camera serves for taking a left image or a stream of images of at least a portion of the left eye of the user, and wherein the right camera takes an image or a stream of images of at least a portion of a right eye of the user. In the following any eye camera in excess of 1 is also called further eye camera.

In case of a head-wearable device, the eye camera(s) can be arranged at the spectacles body in inner eye camera placement zones and/or in outer eye camera placement zones, in particular wherein said zones are determined such that an appropriate picture of at least a portion of the respective eye can be taken for the purpose of determining one or more gaze- or eye-related parameters. In particular, the cameras may be arranged in a nose bridge portion and/or in a lateral edge portion of the spectacles frame, such that an optical field of a respective eye is not obstructed by the respective camera. For example, the cameras can be integrated into a frame of the spectacles body and thereby being non-obstructive.

Typically, in a head-wearable device, a left eye camera and a right eye camera are arranged at least substantially mirror-symmetric with respect to the middle plane.

Furthermore, the device may have illumination means for illuminating the left and/or right eye of the user, in order to increase image data quality, in particular if the light conditions within an environment of the spectacles device are not optimal. Infrared (IR) light may be used for this purpose. Accordingly, the recorded eye image data does not necessarily need to be in the form of pictures as visible to the human eye, but can also be an appropriate representation of the recorded (filmed) eye(s) in a range of light non-visible for humans.

The eye camera(s) is/are typically of known camera intrinsics. As used herein, the term "camera of known camera intrinsics" shall describe that the optical properties of the camera, in particular the imaging properties (imaging characteristics) of the camera are known and/or can be modelled using a respective camera model including the known intrinsic parameters (known intrinsics) approximating the eye camera producing the eye images. Typically, a pinhole camera model is used and full perspective projection is assumed for modelling the eye camera and imaging process. The known intrinsic parameters may include a focal length of the camera, an image sensor format of the camera, a principal point of the camera, a shift of a central image pixel of the camera, a shear parameter of the camera, and/or one or more distortion parameters of the camera.

The parameter of the subject's eye typically refers to an eyeball and/or a pupil of the subject's eye.

In particular, the parameter of the eye may refer to and/or be a center of the eyeball, in particular a center of rotation of the eyeball or an optical center of the eyeball, and/or a gaze- or eye-related parameter of the eye.

The parameter of the eye may as well refer to and/or be a measure of the pupil size of the eye, such as a pupil radius, a pupil diameter or a pupil area.

The gaze- or eye-related parameter may be a gaze-direction related parameter, an iris diameter, a cornea characteristic of at least one eye, a cornea radius, an eyeball radius, a distance pupil-center to cornea-center, a distance cornea-center to eyeball-center, a distance pupil-center to limbus center, a cornea keratometric index of refraction, a cornea index of refraction, a vitreous humor index of refraction, a distance crystalline lens to eyeball-center, a cornea center and/or to corneal apex, a crystalline lens index of refraction, a degree of astigmatism, a limbus major and/or minor axes orientation, an eye cyclo-torsion, an eye intra-ocular distance, an eye vergence, a statistics over eye adduction and/or eye abduction, and a statistics over eye elevation and/or eye depression, data about drowsiness and/or awareness of the user, parameters for user iris verification and/or identification.

The gaze-direction related parameter may be a gaze direction, a cyclopean gaze direction, a 3D gaze point, a 2D gaze point, a visual axis orientation, an optical axis orientation, a pupil axis orientation, and a line of sight orientation of the user.

Gaze- or eye-related parameters, points and directions are typically determined with respect to a coordinate system that is fixed to the eye camera(s) and/or the device.

For example, (a) Cartesian coordinate system(s) defined by the image plane(s) of the eye camera(s) may be used.

Parameters, points and directions may also be specified or determined within and/or converted into a device coordinate system, a head coordinate system, a world coordinate system or any other suitable coordinate system.

In particular, if the device comprises more than one eye camera and the relative poses, i.e. the relative positions and orientations of the eye cameras, are known, geometric quantities like points and directions which have been specified or determined in any one of the eye camera coordinate systems can be converted into a common coordinate system. Relative camera poses may be known because they are fixed by design, or because they have been measured after each camera has been adjusted into it's use position.

In one embodiment, a method for generating data suitable for determining a parameter of at least one eye of a subject, the eye comprising an eyeball and an iris defining a pupil, includes receiving image data of an eye at a first time from a camera of known camera intrinsics, which camera defines an image plane. A first ellipse representing a border of the pupil of the eye at the first time is determined in the image data. The camera intrinsics and the first ellipse are used to determine a 3D orientation vector of a first circle in 3D and a first center line on which a center of the first circle is located in 3D, so that a projection of the first circle, in a direction parallel to the first center line, onto the image plane is expected to reproduce the first ellipse at least substantially, i.e. reproduces the first ellipse with high accuracy, i.e. with an error of less than 5% or even less than 2%. A first eye intersecting line in 3D expected to intersect a 3D center of the eyeball at the first time is determined as a line which is, in the direction of the orientation vector, parallel-shifted to the first center line by an expected distance between the center of the eyeball and a center of the pupil.

Accordingly, the first eye intersecting line, which limits the position of the center of the eyeball to a line and thus can be considered as a parameter of the eye, can be determined without using glints or markers and with low calculation costs, low numerical effort and/or very fast. This even allows determining the parameters of an eye in real time (within sub-milliseconds range per processed image) with comparatively low hardware requirements. Accordingly, parameter(s) of the eye may be determined with hardware that is integrated into a head-wearable device during taking eye images with the camera of the head-wearable device and with a negligible delay only, respectively with hardware of low computational power, like smart devices, connectable to the head-wearable device.

Note that the process of determining the orientation vector of the first circle and the first center line is typically done similar as explained in reference [1]. Reference [1] describes a method of 3D eye model fitting and gaze estimation based on pupil shape derived from (monocular) eye images. Starting from a camera image of an eye and having determined the area of the pupil represented by an ellipse, the first step is to determine the circle in 3D space, which gives rise to the observed elliptical image pupil, assuming a (full) perspective projection and known camera parameters. If this circle is found, it can serve as an approximation of the actual pupil of the eye, i.e. the approximately circular opening of varying size within the iris. Mathematical methods for achieving this "unprojection" give rise to two ambiguities: firstly, there are two solution circles for a given fixed circle radius on the cone which represents the space of all possible solutions. Deciding which one is a correct pupil candidate is described in reference [1]. The second ambiguity is a size-distance ambiguity, which is the harder one to resolve: given only a 2D image it is not possible to know a priori whether the pupil is small and close to the camera or large and far away from the camera. The second ambiguity is resolved in reference [1] by generating a model which comprises 3+3N parameters, including the 3 eyeball center coordinates and parameters of pupil candidates extracted from a time series of N camera images. This model is then optimized numerically in a sophisticated iterative fashion to yield the final eyeball center coordinates.

Compared to reference [1], the proposed solution herein for resolving the size-distance ambiguity (which is based on the proposed eye intersecting line(s)) represents a considerable conceptual and computational simplification. This allows determining parameters of (an) eye(s) such as eyeball position(s), pupil size(s) and gaze direction(s) in real-time with considerably reduced hardware and/or software requirements. Accordingly, lightweight and/or comparatively simple head-wearable devices may be more broadly used for purposes like gaze-estimation and/or pupillometry, i.e. measuring the actual size of the pupil in physical units of length.

Note that the method does not require taking into account a glint from the eye for generating data suitable for determining the parameter of the eye. In other words, the method may be glint-free. Therefore, the method does not require using structured light and/or special purpose illumination to derive parameters of the eye.

Note further that eyes within a given species, e.g. humans, only vary in size within a very narrow margin and many physiological parameters can thus be assumed constant/equal between different subjects, which enables the use of 3D models of an average eye for the purpose of determining variable or situation dependent gaze- or eye-related parameters. An example for such a physiological parameter is the distance R between center of the eyeball, in the following also referred to as eyeball center, and center of the pupil, in the following also referred to as pupil center. In human eyes the distance R can be assumed with high accuracy as a constant (R=10.39 mm), which can therefore be used as the expected distance in a 3D model of the human eye for calculating parameters of the eye. Alternatively, an individual value may be used for the subject or even for a particular eye, if such value has been measured in advance.

Therefore, in an embodiment of a method, the expected value R can be used to construct an ensemble of possible eyeball center positions (a 3D eye intersecting line), based on an ensemble of possible pupil center positions (a 3D center line) and a 3D orientation vector of the ensemble of possible 3D pupil circles, by parallel-shifting the 3D center line by the expected distance R between the center of the eyeball and a center of the pupil along the direction of the 3D orientation vector.

Each further image/observation of one and the same eye but with a different gaze direction gives rise to an independent eye intersecting line in 3D. Finding the nearest point between or intersection of at least two independent eye intersecting lines thus yields the coordinates of the eyeball center in a non-iterative manner. This provides considerable conceptual and computational simplification over prior art methods. The need though remains, as with the prior art methods, to acquire a time series of N>1 eye images/observations and the method requires those observations to show the eye under a relatively large variation of gaze angles in order for the intersection of those N eye intersecting lines to provide a reliable eyeball center calculation.

Accordingly, a method for determining a parameter of an eye typically includes receiving image data of a further eye of the subject at a second time, substantially corresponding to the first time, from a camera of known camera intrinsics and defining an image plane, the further eye comprising a further eyeball and a further iris defining a further pupil, determining a further ellipse in the image data, the further ellipse at least substantially representing the border of the further pupil of the further eye at the second time, using the camera intrinsics and the further ellipse to determine a 3D orientation vector of a further circle in 3D and a further center line on which a center of the further circle is located in 3D, so that a projection of the further circle, in a direction parallel to the further center line, onto the image plane is expected to reproduce the further ellipse, and determining a further eye intersecting line in 3D expected to intersect a 3D center of the further eyeball at the second time as a line which is, in the direction of the 3D orientation vector of the further circle, parallel-shifted to the further center line by an expected distance between the center of the further eyeball and a center of the further pupil.

In other words, instead of a purely monocular paradigm, image data from more than one eye of the subject, recorded substantially simultaneously can be leveraged in a binocular or multiocular setup.

Typically, the respective images of an/each eye which are used to determine the eye intersecting lines are acquired with a frame rate of at least 25 frames per second (fps), more typical of at least 30 fps, more typical of at least 60 fps, and more typical of at least 120 fps or even 200 fps.

In this way, in case image data from one eye originates from a different eye camera than image data from a further eye, it can be guaranteed that eye observations are sufficiently densely sampled in time in order to provide substantial simultaneous image data of different eyes. Image frames stemming from different cameras can be marked with timestamps from a common clock. This way, for each image frame recorded by a given camera at a (first) time t, a correspondingly closest image frame recorded by another camera at a (second) time t' can be selected, such that abs(t−t') is minimal (e.g. at most 2.5 ms if cameras capture image frames at 200 fps).

In case image data from one eye and from a further eye originates from the same camera, the second time can naturally correspond exactly to the first time, in particular the image data of the eye and the image data of the further eye can be one and the same image comprising both (all) eyes.

According to a preferred embodiment, a method includes using the first eye intersecting line and the further eye intersecting line to determine expected coordinates of the center of the eyeball and of the center of the further eyeball, such that each eyeball center lies on the respective eye intersecting line and the 3D distance between the eyeball centers corresponds to a predetermined value (IED, IPD), in particular a predetermined inter-eyeball or inter-pupillary distance.

According to this embodiment, the centers of both eyeballs of a subject may be determined simultaneously, based on a binocular observation at merely a single point in time, instead of having to accumulate a time series of N>1 observations. Also, no monocular intersection of eye intersecting lines needs to be performed and the method thus works under entirely static gaze of the subject, on a frame by frame basis. This is made possible by the insight that the distance between two eyes of a subject can be considered another physiological constant and can thus be leveraged for determining parameters of one or more eye of a subject in the framework of an extended 3D eye- and head-model.

The predetermined distance value (IED, IPD) between the center of the eyeball and the center of the further eyeball can be an average value, in particular a physiological constant or population average, or an individually measured value of the subject. The average human inter-pupillary distance (IPD) at fixation at infinity can be assumed as IPD=63.0 mm. This value is therefore a proxy for the actual 3D distance between the eyeball centers of a subject, the inter-eyeball distance (IED) Individually measuring the IPD can for example be performed with a simple ruler.

In a particularly preferred embodiment, the expected coordinates of the center of the eyeball and of the center of the further eyeball are determined, such that the radius of the first circle in 3D, representing the pupil of the eyeball, and the radius of the further circle in 3D, representing the further pupil, are substantially equal. As a further insight, it is possible to leverage the physiological fact that in most beings, pupils of different eyes are controlled by the same neural pathways and can not change size independently of each other. In other words, the pupil size of the left and of the right eye of for example a human is substantially equal at any instant in time.

Visualizing the binocular geometric 3D setup provided by the 3D circle and further circle, 3D center line and further center line, 3D eye intersecting line and further eye intersecting line and choosing a predetermined inter-eye distance, it will be shown that requesting the size of the circle and the size of the further circle in 3D to be equal provides an unambiguous solution which yields both 3D eyeball center positions as well as the pupil size with merely a single binocular observation in time.

This non-iterative method is numerically stable, especially under static gaze conditions, and extremely fast and can be performed on a frame by frame basis in real-time. Alternatively, to be more robust to noise, observations can be averaged over a given time span. Once the center of an eyeball is known, other parameters of the eye such as an expected gaze direction, optical axis, orientation, visual axis of the eye, size or radius of the pupil of the eye can be calculated (also non-iteratively) for subsequent observations at later instants in time, simply based on the "unprojection" of pupil ellipse contours, providing even faster computation.

In particular, an expected gaze direction of the respective eye may be determined as a vector which is antiparallel to the respective circle orientation vector.

Alternatively and/or in addition, effects of refraction by the cornea may be taken into account.

According to an embodiment, a method for determining a correction function taking into account corneal refraction to correct at least one parameter of at least one eye of the subject includes calculating, using the known camera intrinsics, synthetic camera images of several model eyeballs of at least one eye with varying effective corneal refraction index ($n_{ref}$), for a plurality of given values of the at least one parameter of the model eyeballs. The synthetic camera images are used to determine (calculate) expected values of the one or more parameters of the at least one eye, using any of the methods as described herein for doing so. The expected (calculated) values and the corresponding given (ground truth) values of the at least one parameter are then used to determine a correction function, which maps, depending on the effective corneal refraction index ($n_{ref}$), the expected values of the at least one parameter to the respective given values of the at least one parameter.

The given values typically include coordinates of respective centers of the model eyeballs, given radii of a pupil of the model eyeballs and/or given gaze directions of the model eyeballs. These given values thus constitute the ground truth values, which a method for determining them should output.

Determining the expected (calculated) values typically includes determining respective (pupil circle) 3D center lines and 3D eye intersecting lines expected to intersect the center of the respective model eyeball for the plurality of given coordinates of respective centers of the model eyeballs, given radii of a pupil of the model eyeballs and/or given gaze directions, i.e. for all the synthetic camera images.

Determining the correction function may be achieved using a multivariate polynomial regression analysis.

Calculating the synthetic camera images may be achieved by raytracing an arrangement of a camera model, which describes the camera, and 3D model eyeballs arranged in the field of view of the camera model.

According to embodiments, a respective two-sphere 3D eye model may be used as model eyeballs. For example, the so-called LeGrand eye model (see reference [1]), or the so-called Navarro eye model (see reference [2]) may be used for modelling eyeballs and calculating synthetic images, respectively.

The model of the camera typically includes a focal length, a shift of a central image pixel, a shear parameter, and/or one or more distortion parameters of the camera. The camera may be modelled as a pinhole camera.

The correction function is typically stored and may later be used to correct one or more parameters of at least one eye determined from respective eye images. In particular, a corrected value for the center of the eyeball of the eye, the expected gaze direction, the expected optical axis, the expected orientation, the expected visual axis, and/or the expected size or radius of the pupil of the eye may be calculated using the correction function.

The correction function may be designed to take as input at least one parameter of one eye only, or may take as joint input parameters from several eyes.

Note that determining the respective (pupil circle) center line as described herein is based on the unprojection of the image ellipse using the known camera model. Different thereto, determining the respective eye intersecting line is based on the thus derived centre line and an eye model, typically a 3D eye model. In the simplest case and without correcting the corneal refraction effects, the eye model may only have one parameter, namely the expected distance R between the center of the eyeball and the center of the pupil.

According to an embodiment, a system comprises a device and a computing and control unit, the device including at least one camera of known camera intrinsics for producing image data including at least one eye of a subject. The (each) camera comprises a sensor defining an image plane. The computing and control unit is configured to receive image data of at least one eye at a first time from at least one camera, determine a first ellipse in the image data, the first ellipse at least substantially representing a border of the pupil at the first time, to use the camera intrinsics and the first ellipse to determine a 3D orientation vector of a first circle in 3D and a first center line on which a center of the first circle is located in 3D, so that a projection of the first circle, in a direction parallel to the first center line, onto the image plane is expected to reproduce the first ellipse, and to determine a first eye intersecting line in 3D expected to intersect a 3D center of the eyeball at the first time as a line which is, in the direction of the orientation vector, parallel-shifted to the first center line by an expected distance between the center of the eyeball and a center of the pupil.

Typically, the computing and control unit is configured to perform the methods for generating data suitable for determining at least one parameter of at least one eye of a subject as explained herein.

In a further embodiment, the computing and control unit of the system may be configured to receive image data of a further eye of the subject at a second time, substantially corresponding to the first time, from a camera of known camera intrinsics and defining an image plane. The further eye comprises a further eyeball and a further iris defining a further pupil. The camera may be the single camera of the device, or may be one of several cameras of the device. The computing and control unit is further configured to determine a further ellipse in the image data, the further ellipse at least substantially representing the border of the further pupil of the further eye at the second time, to use the camera intrinsics and the further ellipse to determine a 3D orientation vector of a further circle in 3D and a further center line on which a center of the further circle is located in 3D, so that a projection of the further circle, in a direction parallel to the further center line, onto the image plane is expected to reproduce the further ellipse, and to determine a further eye intersecting line in 3D expected to intersect a 3D center of the further eyeball at the second time as a line which is, in the direction of the 3D orientation vector of the further circle, parallel-shifted to the further center line by an expected distance between the center of the further eyeball and a center of the further pupil.

The computing and control unit may be configured to use the first eye intersecting line and the further eye intersecting line for determining expected coordinates of the center of the eyeball and/or the further eyeball. The further eye intersecting line is typically determined by a method analogous to the one used to determine the first eye intersecting line and for substantially the same point in time, however for a different, further eye.

The expected coordinates of the center of the eyeball and of the center of the further eyeball may be determined such that each eyeball center lies on the respective eye intersecting line and the 3D distance between the eyeball centers corresponds to a predetermined value, in particular a predetermined inter-eyeball distance.

The computing and control unit may be configured to receive the image data of the eye and the image data of the further eye from a single camera of the device or from different cameras the relative poses of which are known, and is further configured to determine at least the respective orientation vectors, center lines and eye intersecting lines with respect to the 3D coordinate system of the respective camera, and/or transform them into a common 3D coordinate system via the known relative camera poses.

A position and/or orientation of the respective camera or cameras of the device may be non-adjustably fixed or adjustable and/or fixable with respect to some reference structure like a frame or housing of the device, in particular such that the relative poses of the cameras are known per construction or can be measured after having been adjusted.

If the device comprises a single camera, adjustable or not, all calculations can be performed in the (3D) coordinate system defined by that camera.

If the device comprises several cameras which are rigidly, non-adjustably fixed with respect to the device, the relative poses of all cameras with respect to each other and/or with respect to some arbitrarily chosen coordinate system of the device are known per construction. In this case calculations based on image data originating from a given camera can first be performed in the respective coordinate system of that camera. This concerns for example points, lines and directions like (pupil circle) center lines and eye intersecting lines. For subsequent calculations for determining one or more parameters of one or more eye, all such quantities can then be transformed into a common 3D coordinate system via the known relative camera poses. This common coordinate system can for example be the coordinate system of one of the (arbitrarily chosen) cameras, or a coordinate system defined by a reference structure of the device, such as a frame or housing.

The computing and control unit may be configured to use a stored correction function taking into account corneal refraction to determine in real-time a corrected value for one or more parameters of one or more eyes, such as the center of an eyeball, the expected gaze direction, the expected optical axis, the expected orientation, the expected visual axis, and the expected size or radius of the pupil of the eye and/or a further eye.

Different thereto, the method for determining a correction function as explained herein is typically performed by a more powerful computing device such as a desktop computer or the like.

The device may be a head-wearable device or a remote eye-tracking device.

The computing and control unit can be at least partly integrated into the device and/or at least partly provided by a companion device of the system, for example a mobile companion device such as a mobile phone, tablet or laptop computer. Both the device and the companion device may have computing and control units, which typically communicate with each other via an interface board (interface controller), for example a USB-hub board (controller). Either of these computing and control units may be solely or partly responsible for determining the one or more gaze- or eye-related parameters of an eye and/or a further eye of the user.

In one embodiment, the head-wearable (spectacles) device is provided with electric power from a companion device of the system during operation of the spectacles device, and may thus not require an internal energy storage such as a battery. Accordingly, the head-wearable (spectacles) device may be particularly lightweight. Further, less heat may be produced during device operation compared to a device with an internal (rechargeable) energy storage. This may also improve comfort of wearing.

The computing and control unit of the head-wearable (spectacles) device is typically arranged non-visible within the spectacles body, in particular in the left lateral portion, in the right lateral portion, in the left holder and/or in the right holder.

The computing and control unit of the head-wearable (spectacles) device may have a USB-hub board, a camera controller board connected with the camera, and a power-IC connected with the camera controller board, the camera and/or the connector for power supply and/or data exchange, and an optional head orientation sensor having an inertial measurement unit (IMU).

All this can be achieved with a lightweight, unobtrusive, very comfortable head-wearable (spectacles) device that may be comparatively easy and cost-effective manufactured and repaired and can even be used as normal glasses (with standard optical lenses) or sun glasses (with detached scene camera(s)) without being easily recognized as an eye tracking device. Furthermore, no particular heat management, physical shields to protect the user, vents or the like are required.

If the device is a head-wearable spectacle like device, placing eye camera(s) in the respective lateral portion or in the nose bridge portion of the spectacles body allows for a very discrete and non-obtrusive camera arrangement in the spectacles body without noticeably obstructing the visible field of the user, and ensures a beneficial view on to the eyeballs of the user. In both cases eye cameras can be fixedly placed in sufficiently rigid structures of the frame or spectacles body such that their relative poses are known per design and reproducible with high accuracy during manufacturing. It is also possible to measure relative camera poses post manufacturing.

In embodiments which comprise head-wearable devices, the typically tiny eye camera(s) are not even noticed by the user when wearing the device. Further, In all embodiments the eye camera(s) may be infrared cameras. IR-light sources part of the device may be used to illuminate the eyes of the user in embodiments referring to IR-cameras. IR-illumination may only be used/invoked when the image quality is too low or expected to be low, for example in a dark environment. IR-illumination may also be on permanently, or always be on and only switched off to save power and/or when image quality is sufficient without illumination.

Reference will now be made in detail to various embodiments, one or more examples of which are illustrated in the figures. Each example is provided by way of explanation, and is not meant as a limitation of the invention. For example, features illustrated or described as part of one embodiment can be used on or in conjunction with other embodiments to yield yet a further embodiment. It is intended that the present invention includes such modifications and variations. The examples are described using specific language which should not be construed as limiting the scope of the appended claims. The drawings are not scaled and are for illustrative purposes only. For clarity, the same elements or steps have been designated by the same references in the different drawings if not stated otherwise.

Figure 1B:
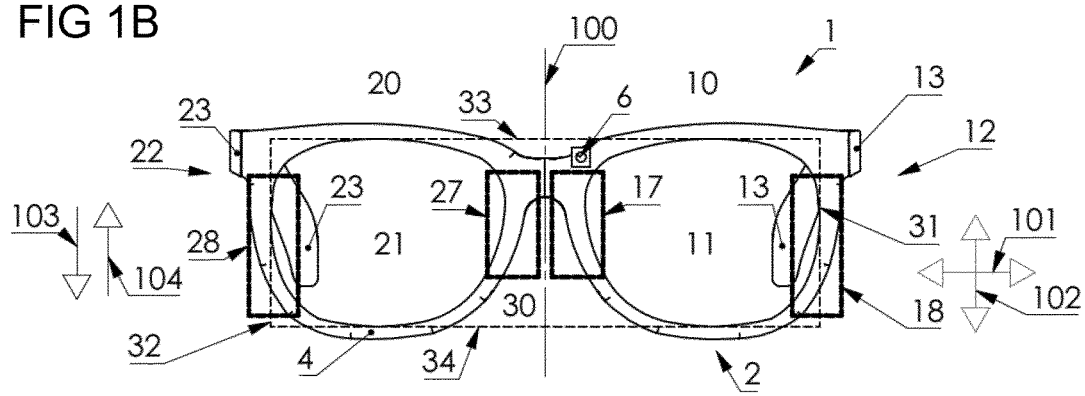
Figure 1C:
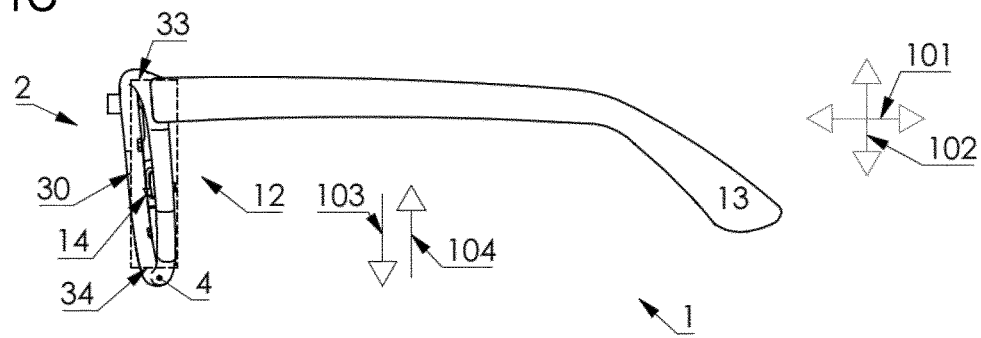

With reference to FIGS. 1A to 1C, a generalised embodiment of a head-wearable spectacles device for determining one or more gaze- or eye-related parameters of a user is shown. In fact, with the help of FIGS. 1A and 1C a plurality of embodiments shall be represented, wherein said embodiments mainly differ from each other in the position of the cameras 14, 24. Thus, the spectacles device 1 is depicted in FIG. 1A with more than one camera 14, 24 per ocular opening 11, 21 only for presenting each embodiment. However, in this embodiment the spectacles device does not comprise more than one camera 14, 24 associated to each ocular opening 11, 21.

FIG. 1A is a view from above on said spectacles device 1, wherein the left side 10 of the spectacles device 1 is shown on the right side of the drawing sheet of FIG. 1A and the right side 20 of the spectacles device 1 is depicted on the left side of the drawing sheet of FIG. 1A. The spectacles device 1 has a middle plane 100, which coincides with a median plane of the user of the spectacles device 1 when worn according to the intended use of the spectacles device 1. With regard to user's intended use of the spectacles device 1, a horizontal direction 101, a vertical direction 102, 100, a direction "up" 104, a direction "down" 103, direction towards the front 105 and a direction towards the back 106 are defined.

The spectacles device 1 as depicted in FIG. 1A, FIG. 1B, and FIG. 1C comprises a spectacles body 2 having a frame 4, a left holder 13 and a right holder 23. Furthermore, the spectacles body 2 delimits a left ocular opening 11 and a right ocular opening 21, which serve the purpose of providing an optical window for the user to look through, similar to a frame or a body of normal glasses. A nose bridge portion 3 of the spectacles body 2 is arranged between the ocular openings 11, 21. With the help of the left and the right holder 13, 23 and support elements of the nose bridge portion 3 the spectacles device 1 can be supported by ears and a nose of the user. In the following, the frame 4 is also referred to as front frame and spectacles frame, respectively.

According to the embodiments represented by FIG. 1A, a left eye camera 14 and/or a right eye camera 24 can be arranged in the spectacles body 2. Generally, the nose bridge portion 3 or a lateral portion 12 and/or 22 of the spectacles body 2 is a preferred location for arranging/integrating a camera 14, 24, in particular a micro-camera. Different locations of the camera(s) 14, 24 ensuring a good field of view on the respective eye(s) may be chosen. In the following some examples are given.

If a camera 14 or 24 is arranged in the nose bridge portion 3 of the spectacles body 2, the optical axis 15 of the left camera 14 may be inclined with an angle $\alpha$ of 142° to 150°, preferred 144°, measured in counter-clockwise direction (or −30° to −38°, preferred −36°) with respect to the middle plane 100. Accordingly, the optical axis 25 of the right camera 24 may have an angle $\beta$ of inclination of 30° to 38°, preferred 36°, with respect to the middle plane 100.

If a position of a camera 14, 24 is located in one of the lateral portions 12, 22 of the spectacles body 2, the optical axis 15 of the left camera 14 may have an angle $\gamma$ of 55° to 70°, preferred 62° with respect to the middle plane, and/or the optical axis 25 of the right camera 24 may be inclined about an angle $\delta$ of 125° to 110° (or −55° to −70°), preferred 118° (or −62°).

Furthermore, a bounding cuboid 30—in particular a rectangular cuboid—may be defined by the optical openings 11, 21, which serves four specifying positions of camera placement zones 17, 27, 18, 28. As shown in FIG. 1A, FIG. 1B, and FIG. 1C the bounding cuboid 30—represented by a dashed line—may include a volume of both ocular openings 11, 21 and touches the left ocular opening 11 with a left lateral surface 31 from the left side 10, the right ocular opening 21 with a right lateral surface 32 from the right side 20, at least one of the ocular openings 11, 21 with an upper surface 33 from above and from below with a lower surface 34.

In case a left/right camera 14, 24 is arranged in the nose bridge portion 3, a projected position of the left camera 14 would be set in a left inner eye camera placement zone 17 and the right camera 24 would be (projected) in the right inner eye camera placement zone 27.

When being in the left/right lateral portion 12, 22, the left camera 14 may be positioned—when projected in the plane of the camera placement zones—in the left outer eye camera placement zone 18, and the right camera 24 is in the right outer eye camera placement zone 28.

With the help of the front view on the spectacles device 1 depicted in FIG. 1B the positions of the eye camera placement zones 17, 18, 27, 28 are explained. In FIG. 1B rectangular squares represent said eye camera placement zones 17, 18, 27, 28 in a vertical plane perpendicular to the middle plane 100.

As a preferred option, all embodiments of the spectacles device 1 as represented by FIG. 1A to 1C have in common, that no more than one camera 14/24 is associated to one of the optical openings 11, 21. Typically, the spectacles device 1 does only comprise one or two cameras 14, 24 to produce image data of a left and a right eyeball 19, 29, respectively.

In the embodiment shown in FIG. 1A to 1C, one camera 14 is arranged for producing image data of one eye 19, while the other camera 24 is arranged for producing image data of a further eye 29. By virtue of the precisely known relative poses of cameras 14 and 24, quantities calculated with respect to the 3D coordinate system defined by one camera can be transformed into the 3D coordinate system defined by the other camera or into a common, e.g. headset 3D coordinate system. The same reasoning applies for embodiments with more than two cameras.

The spectacles device 100 as shown in FIG. 1A comprises a computing and control unit 7 configured for processing the image data from the left and/or the right camera 14, 24 for determining parameter(s) of the respective eye or both eyes.

Typically, the computing and control unit is non-visibly integrated within the holder, for example within the right holder 23 or the left holder 13 of the spectacles device 1. According to a non-shown embodiment, a processing unit can be located within the left holder. Alternatively, the processing of the left and the right images from the cameras 14, 24 for determining the gaze- or eye-related parameter(s) may alternatively be performed by a connected companion device such as smartphone or tablet or other computing device such as a desktop or laptop computer, and may also be performed entirely offline, based on videos recorded by the left and/or right cameras 14, 24.

The head wearable device 1 may also include components that allow determining the device orientation in 3D space, accelerometers, GPS functionality and the like.

The head wearable device 1 may further include any kind of power source, such as a replaceable or rechargeable battery, or a solar cell. Alternatively (or in addition), the head wearable device may be supplied with electric power during operation by a connected companion device, and may even be free of a battery or energy source.

The device of the present invention may however also be embodied in configurations other than in the form of spectacles, such as for example as integrated in the nose piece or frame assembly of an AR or VR head-mounted display (HMD) or goggles or similar device, or as a separate nose clip add-on or module for use with such devices. Also, the device may be a remote device, which is not wearable or otherwise in physical contact with the user.

Figure 2:
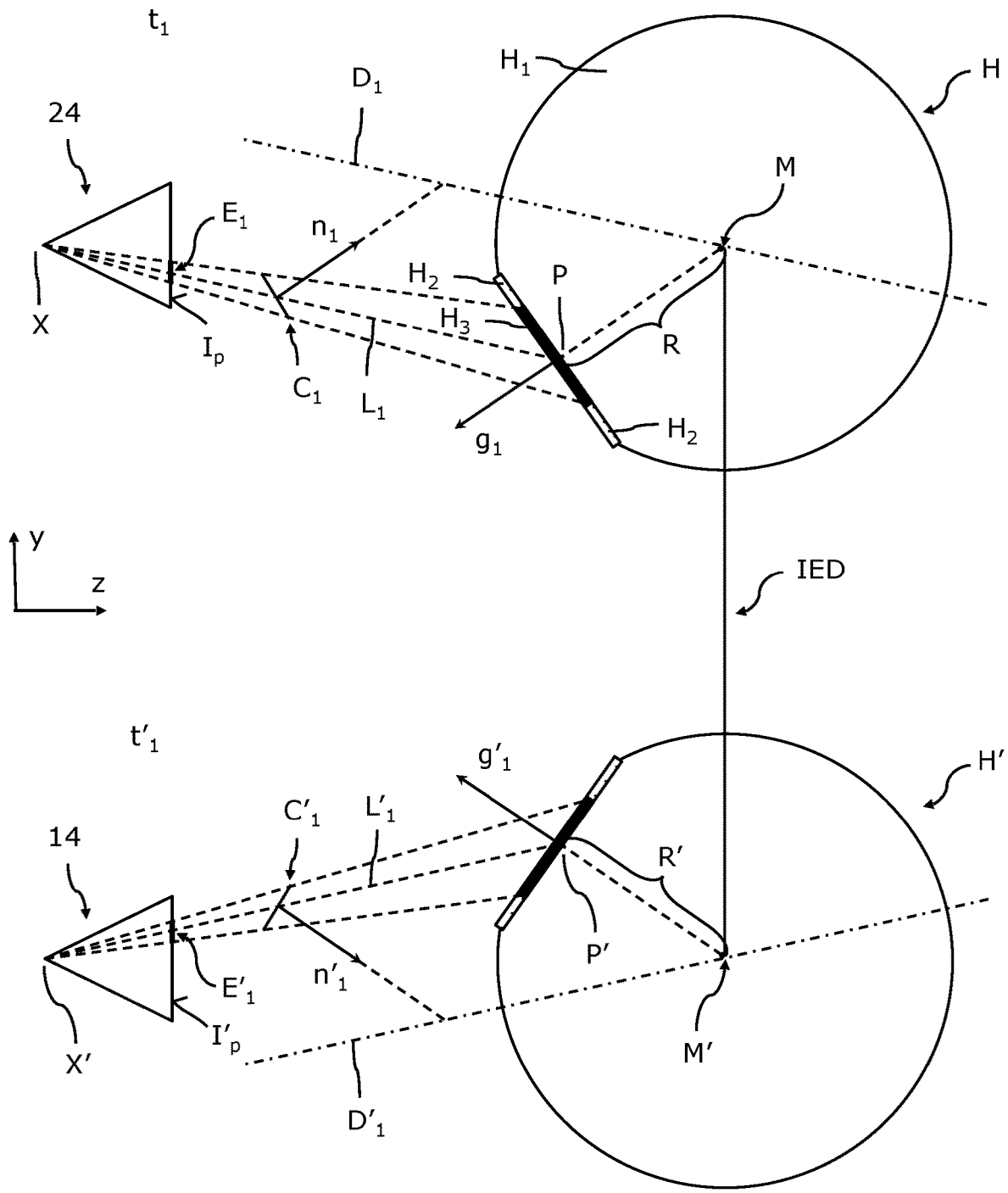
FIG. 2 illustrates geometry used in methods for generating data suitable for determining a parameter of one or more eyes according to embodiments.

FIG. 2 illustrates geometry used in methods for generating data suitable for determining one or more parameters of one or more eyes.

In the exemplary embodiment, the cameras 14 and 24 used for taking images of the user's eyes are modelled as pinhole cameras. The user's eyes H, H' are represented by an appropriate model for human eyes. In particular, a two sphere eye model as illustrated in FIG. 3A may be used.

Figure 3A:
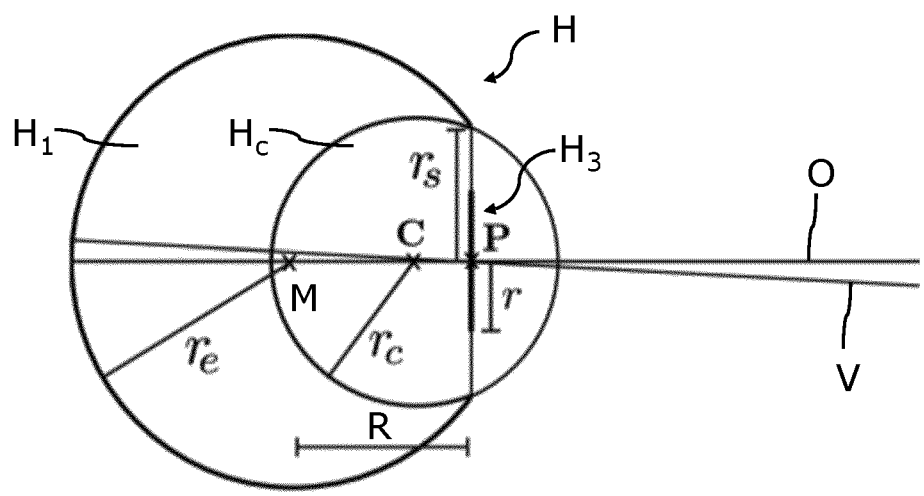
FIG. 3A is a schematic view of an exemplary two-sphere eye model.

FIG. 3A is a schematic view of an exemplary two-sphere model H for human eyes according to LeGrand. It approximates the eye geometry as consisting of two partial spheres. The larger partial sphere $H_1$ corresponds to the eyeball with center at position M and radius of curvature $r_e$. The second partial sphere Hc represents the cornea with center C and radius of curvature $r_c$. It is assumed that the cornea and the aqueous humor form a continuous medium with a single effective refractive index, $n_{ref}$. While the effective refractive index of the cornea varies slightly across the human population, it is reasonable to assume it to be fixed to the physiologically plausible value $n_{ref}=1.3375$. The iris and pupil $H_3$ within the LeGrand eye model are two circles with radius $r_s$ and r, respectively, sharing the same center P lying at a distance $R=(r_e^2-r_s^2)^{0.5}$ from M along the direction MC. Their normal directions coincide, are parallel to MC, and thus correspond to the optical axis O of the eye. For calculation the following physiologically plausible values can be assumed: eyeball radius of curvature $r_e=12$ mm, cornea radius $r_c=7.8$ mm, and iris radius $r_s=6$ mm. The pupil radius r typically varies in the physiologically plausible range of approximately 0.5-4.5 mm.

FIG. 2 illustrates cameras 14, 24 and the human eyes H', H in the respective fields of view of the cameras 14, 24. Determining of (pupil circle) center lines L and eye intersecting lines D will be explained based on one side and camera first (monocularly), the calculations for the other side/camera being analogous. Thereafter, a binocular scenario will be explained. The cameras 14, 24 are typically near-eye cameras as explained above with regard to FIGS. 1A to 1C. For the sake of clarity, a Cartesian coordinate system y, z is additionally shown (x-axis perpendicular to paper plane). We will assume this to be a common 3D coordinate system into which all quantities originally calculated with respect to an individual camera's coordinate system can be or have been transformed.

In gaze estimation, estimating the optical axis O of the eye is a primary goal. In pupillometry, estimating the actual size (radius) of the pupil in units of physical length (e.g. mm) is the primary goal. The state of the eye model, similar to the one employed by reference [1], which is incorporated by reference in its entirety, is uniquely determined by specifying the position of the eyeball center M and the pose and radius of the pupil $H_3=(\varphi, \theta, r)$, where $\varphi$ and $\theta$ are the spherical coordinates of the normalized vector pointing from M into the direction of the center of corneal curvature C. We will refer to $\varphi$ and $\theta$ as gaze angles. In some cases, we will also refer to the angle between the optical axis O and the negative z-axis as gaze angle. To determine the eyeball center M is therefore a necessary first step in video image based, glint-free gaze estimation and pupillometry.

In reference [1], a complex iterative optimization is performed to estimate eyeball positions as well as gaze angles and pupil size based on a time series of observations. Different thereto, a computationally less demanding process is proposed herein.

In particular, as a first step a first ellipse $E_1$ representing a border (outer contour) of the pupil $H_3$ at the first time $t_1$ is determined in a first image taken with the camera 24. This is typically achieved using image processing techniques.

As explained in detail in reference [1] a camera model of the camera 24 is used to determine an orientation vector $n_1$ of the first circle $C_1$ and a first center line $L_1$ on which a center of the first circle $C_1$ is located, so that a projection of the first circle $C_1$, in a direction parallel to the first center line $L_1$, onto the image plane $I_p$ reproduces the first ellipse $E_1$ in the image. In this step, the same disambiguation procedure on pairs of un-projected circles as proposed in reference [1] (see FIG. 3 and corresponding description of [1]) may be used.

As a result, we obtain circle $C_1$, which we can choose as that circle along the un-projection cone which has radius r=1.0 mm, and its orientation vector $n_1$ in 3D. We will call $c_1$ the vector from the camera center X (the center of the perspective projection) to the center of this circle $C_1$ of radius r=1.0 mm, i.e. $c_1=C_1-X$. The center line can then be written as $L_1(r)=r*c_1$ with r taking any positive real value. Note that vector $c_1$ does not necessarily have length equal to 1.

However, the size-distance ambiguity explained above remains so far. It is this size-distance ambiguity which is resolved in a much simpler manner than proposed in [1] by the methods of the present disclosure.

For this purpose, a first eye intersecting line $D_1$ expected to intersect the center M of the eyeball at the first time $t_1$ may be determined as a line which is, in the direction of the orientation vector $n_1$, parallel-shifted to the first center line $L_1$ by the expected distance R between the center M of the eyeball and the center P of the pupil. As already explained above, the expected distance R may be set to its average human (physiological) value R=10.39 mm, which is in the following also referred to as a physiological constant of human eyes.

To this end, note that for each choice of pupil radius r, the circle selected by $r*c_1$ constitutes a 3D pupil candidate that is consistent with the observed pupil ellipse $E_1$. In the framework of the two-sphere model, if the circle thus chosen were to be the actual pupil, it would thus need to be tangent to a sphere of radius R and position given by $$D_1(r) = r*c_1 + R*n_1 \quad \text{(Eq.1)}$$

defining a line in 3D that is parametrized by pupil radius r, in which $r*c_1$ represents the ensemble of possible pupil circle centers, i.e. the circle center line $L_1$. Note that $n_1$ is normalized to length equal 1, but vector $c_1$ is not, as explained above. As the center of the 3D pupil $P=r*c_1$ when r is chosen to be the actual pupil radius, the actual eyeball center M thus indeed needs to be contained in this line $D_1$.

Note also that it is a property of perspective projection, that the center of the ellipse $E_1$ in the camera image, which ellipse is the result of perspective projection of any of the possible 3D pupil circles corresponding to $r*c_1$, does not lie on the circle center line $L_1$.

Providing such eye intersecting lines D thus constitutes a method for generating data suitable for determining one or more parameters of at least one eye of a subject in a more simple and computationally more efficient and therefore faster way.

In a monocular method, a second ellipse $E_2$ representing the border of the pupil $H_3$ at a second time $t_2$ can be determined in a second image taken with the camera 24. Likewise, the camera model may be used to determine an orientation vector $n_2$ of the second circle $C_2$ and a second center line $L_2$ on which a center of the second circle $C_2$ is located, so that a projection of the second circle $C_2$, in a direction parallel to the second center line $L_2$, onto the image plane $I_p$ of the camera reproduce the second ellipse $E_2$ in the image. Likewise, a second eye intersecting line $D_2$ expected to intersect the center M of the eyeball at the second time $t_2$ may be determined as a line which is, in the direction of the orientation vector $n_2$, parallel-shifted to the second center line $L_2$ by the distance R. Therefore, since the center M of the eyeball has to be contained in both $D_1$ and $D_2$, it may be determined as intersection point of the first eye intersecting line $D_1$ and the second eye intersecting line $D_2$ or as nearest point to the first eye intersecting line $D_1$ and the second eye intersecting line $D_2$. Note that each un-projection circle $C_k$ constrains the eyeball position M in 3D to the respective line $D_k$ (the subscript k indicates a time or observation index, with k=1 in FIG. 2). Typically, the eye intersecting lines $D_k$ may be determined for a plurality of different times $t_k$ with k=1 ... n. Each of the eye intersecting lines $D_k$ is expected to intersect the center M of the eyeball at respective times. Therefore, the center M of the eyeball is typically determined as nearest point <M> to the eye intersecting lines $D_k$, k=1 ... n. In other words, in this monocular method, the center M of the eyeball intersection is in practice typically taken in a least-squares sense. After determining the eyeball position M, gaze directions $g_1$, $g_2$ may be determined as being negative to the respective orientation vector $n_1$, $n_2$. The pupil radius r for each observation k can simply be obtained by scaling $r*c_k$ such that the resulting circle is tangent to the sphere centered at M and having radius R. Further, the respective optical axis may be determined as by (normalized) direction from P to the intersection point M.

Figure 3B:
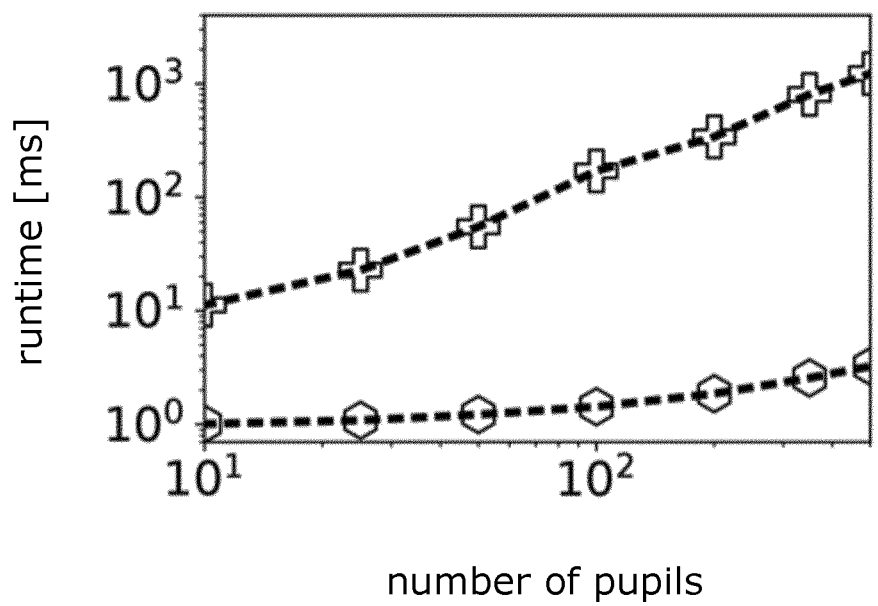
FIG. 3B illustrates the computational runtime of methods for determining a parameter of an eye.

As illustrated in FIG. 3B, the number of pupils (image frames) that can be calculated with the monocular method explained above (method A) is, for the same computing hardware, typically at least one order of magnitude higher compared to the method of reference [1].

In an embodiment of a binocular method (method C), referring again to FIG. 2, the same procedure for generating a 3D circle center line and a 3D eye intersecting line as explained for eyeball H with center M based on image data from camera 24 can be applied to a further eye H' with center M', based on image data from camera 14, at a second time ($t'_1$), substantially corresponding to the first time ($t_1$), yielding corresponding quantities for the further eye, which are denoted with a prime (') in the figure.

The expected (constant) distance R' between the center of the eyeball M' and the center of the pupil P' of the further eye H' may be set equal to the corresponding value R of eye H, or may be an eye-specific value.

In a preferred embodiment, a method further comprises using the first eye intersecting line $D_1$ and the further eye intersecting line $D'_1$ to determine expected coordinates of the center M of the eyeball H and of the center M' of the further eyeball H', such that each eyeball center lies on the respective eye intersecting line and the 3D distance between the eyeball centers corresponds to a predetermined value (IED, IPD), in particular a predetermined inter-eyeball distance IED. This embodiment is based on the insight that the distance between two eyes of a grown subject changes very little if at all over time and can thus be entered into the method as a further physiological constraint, thus narrowing down the space of possible solutions for finding parameters of one of more eyes, such as the 3D eyeball centers.

In particular, the predetermined distance value (IED, IPD) between the center of the eyeball and the center of the further eyeball may be an average value, in particular a physiological constant or population average, or an individually measured value of the subject. The average human inter-pupillary distance (IPD) at fixation at infinity can be assumed as IPD=63.0 mm. This value is therefore a proxy for the actual 3D distance between the eyeball centers of a human subject, the inter-eyeball distance (IED) Individually measuring the IPD can for example be performed with a simple ruler.

In this example, the center of the eyeball and the center of the further eyeball can for example be found based on some assumption about the geometric setup of the device with respect to the eyes and head of the subject, for example that the interaural axis has to be perpendicular to some particular direction, like for example the z-axis of a device coordinate system such as shown in the example of FIG. 2.

In a particularly preferred embodiment, a method further comprises determining the expected coordinates of the center M of the eyeball and of the center M' of the further eyeball, such that the radius r of the first circle in 3D and the radius r' of the further circle in 3D are substantially equal, thereby also determining said radius. As previously set out, the center of the 3D pupil P=r*$c_1$ when r is chosen to be the actual pupil radius. The same applies to the further eye, where P'=r'*$c'_1$, with $c'_1$ being the vector from the camera center X' to the center of this circle $C'_1$ of radius r=1.0 mm, i.e. $c'_1$=$C'_1$−X'.

As a physiological fact, in most beings pupils of different eyes are controlled by the same neural pathways and can not change size independently of each other. In other words, the pupil size of the left and of the right eye of for example a human is substantially equal at any instant in time. This insight was surprisingly found to enable a particularly simple and fast solution to both the gaze-estimation (3D eyeball center and optical axis) and pupillometry (pupil size) problems, in a glint-free scenario based on a single observation in time of two eyes as follows. Since the center coordinates of the eyeball can be determined as $$M = X + r * c_k + R * n_k$$

with r being the actual (but so far unknown) pupil radius, and correspondingly for the further eye, with primed quantities, at any given time $t_k \sim t'_k$, one arrives at the condition for the distance ||M−M'|| between the eyeball centers $$||(X + r * c_k + R * n_k) - (X' + r' * c'_k + R' * n'_k)|| = IED \quad (Eq. 2)$$

in which ||.|| denotes the length or norm of a vector. If one makes the physiologically plausible assumptions that R=R' (eyeballs of equal size, this is optional though) and r=r' (pupil radii are equal in both eyes at any given time), (Eq. 2) can be rewritten $$||a + r * b|| = IED$$

where a:=X−X'+R*($n_k$−$n'_k$) and b:=$c_k$−$c'_k$. This leads to a quadratic equation for pupil radius r, which has the solutions $$r_{1,2} = (-a \cdot b \pm sqrt((a \cdot b)^2 - ||b||^2 * (||a||^2 - IED^2))) / ||b||^2 \quad (Eq. 3)$$

with sqrt( ) signifying the square root operation and (a·b) signifying the dot product between these two vectors. The right side of (Eq. 3) only contains known or measured quantities.

Which of the two solutions is the correct pupil radius can be easily decided either based on comparison with physiologically possible ranges (e.g. r>0.5 mm and r<4.5 mm) and/or based on the geometric layout of the cameras and eyeballs. In FIG. 2 for example, there would be a second solution at which eye intersecting lines $D_1$ and $D'_1$ comprise points M and M' at a distance of IED from each other, outside of the figure to the right, corresponding to the larger of one of the two values $r_{1,2}$, and for which the eyes would actually have swapped places. In this scenario, the smaller of values $r_{1,2}$ is therefore always the correct solution.

All the above calculations are performed with respect to a common 3D coordinate system, which can be the 3D coordinate system defined by a single camera of the device, or any other arbitrarily chosen coordinate system into which quantities have been transformed via the known relative camera poses, as is the case in the example of FIG. 2.

Therefore, in this embodiment a particularly simple and even faster solution for calculating all of the 3D eyeball centers, the optical axes (gaze vectors $g_k$, $g'_k$, which are antiparallel to $n_k$, $n'_k$ respectively) and the (joint) pupil size of both eyes is provided in a glint-free scenario based on merely a single observation in time of two eyes of a subject.

Figure 4A:
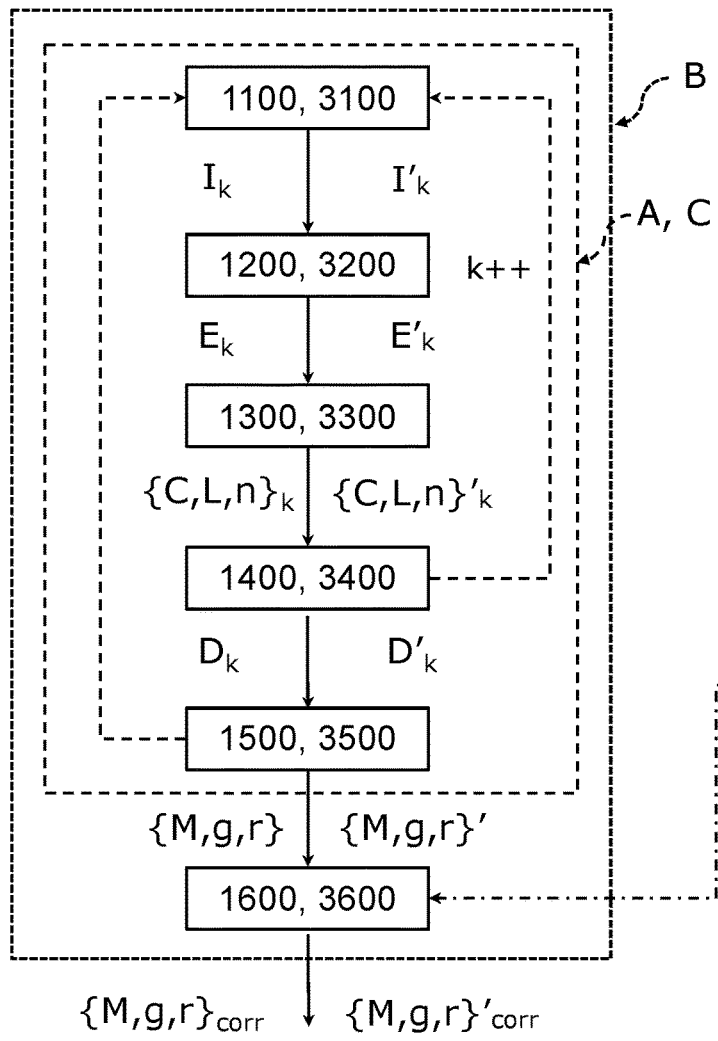
FIG. 4A illustrates flow charts of methods for generating data suitable for determining a parameter of one or more eyes according to embodiments.

FIG. 4A illustrates a flow chart of a method 1000 for generating data suitable for determining one or more parameters of an eye according to embodiments. As indicated by the dashed rectangle A, the method 1000 may at least substantially correspond to the monocular method A explained above. In a first step 1100, an image $I_k$ of the user's eye may be taken by an eye camera of a device at a time $t_k$. In a subsequent step 1200, an ellipse $E_k$ representing a border of the eye's pupil at the time $t_k$ may be determined. In a subsequent step 1300, a camera model describing the camera of the device is used to determine an orientation vector $n_k$ of a circle $C_k$ and a center line $L_k$ on which a center of the circle $C_k$ is located, so that a projection of the circle $C_k$, in a direction parallel to the center line $L_k$, onto an image plane of the camera reproduces the ellipse $E_k$. Thereafter, the center line $L_k$ may be parallel-shifted by an expected distance R between the center of the eyeball and a center of the pupil in the direction of the orientation vector to determine an eye intersecting line $D_k$ which intersects a center M of the user's eyeball at the time $t_k$ in step 1400. As indicated by the right dashed arrow in FIG. 4A, the index k may be incremented and a new cycle 1100 to 1400 of determining eye intersecting line $D_k$ may be started. Thereafter, the center M of the eyeball may be determined as (least square) intersection point of the eye intersecting lines $D_k$, with k=1 . . . n, in step 1500. As indicated by the left dashed arrow in FIG. 4A, the procedure may be repeated at a later time ($t_m$>$t_n$) again, for example after movement of the camera with respect to the eye is detected or expected to have happened. Further, other parameter(s) of the user's eye such as gaze direction g and pupil size r may be determined when the centre M of the eyeball is known. Furthermore, the other parameter(s) of the user's eye may also be determined for later times without recalculating the center M (to save computational time).

FIG. 4A also illustrates a flow chart of a method 3000 for generating data suitable for determining one or more parameters of more than one eye according to embodiments. As indicated by the dashed rectangle C, the method 3000 may at least substantially correspond to the binocular method C explained above with regard to FIG. 2. Since the first steps of method 3000 are entirely analogous to the steps of method 1000, only based on image data of two eyes instead of one eye, corresponding reference numbers are used. Dashed quantities represent those of the second or further eye, as in FIG. 2.

In a first step 3100, an image $I_k$ of a user's eye and an image $I'_k$ of a user's further eye may be taken by one or more eye cameras of a device at a time $t_k \sim t'_k$. In a subsequent step 3200, ellipses $E_k$, $E'_k$ representing borders of the eyes' pupils at the time $t_k$ are determined. In subsequent steps 3300 and 3400, orientation vectors $n_k$, $n'_k$ of circles $C_k$, $C'_k$, center lines $L_k$, $L'_k$ and eye intersecting lines $D_k$, $D'_k$ are determined as previously described.

Different to method 1000 however, in method 3000 a pair of eye intersecting lines $D_k$, $D'_k$ from a single time index k may be used to determine the centers M, M' of the eyeballs together with the corresponding gaze vectors g, g' and pupil radii r, r' or common pupil radius r=e, in step 3500. The iteration over several time steps (k++, right dashed arrow) is therefore not needed in method 3000.

As indicated by the left dashed arrow in FIG. 4A, the procedure in method 3000 may optionally be repeated at a later time ($t_m > t_1$) again (or even continuously), for example after movement of the camera(s) with respect to the eye(s) is detected or expected to have happened. Further, other parameter(s) of the user's eyes such as gaze direction(s) g, g' and pupil size r, r' may be determined when the centres M, M' of the eyeballs are known. These other parameter(s) of the user's eyes may therefore also be determined for later times without recalculating the centers M, M' (to save computational time).

Figure 4B:
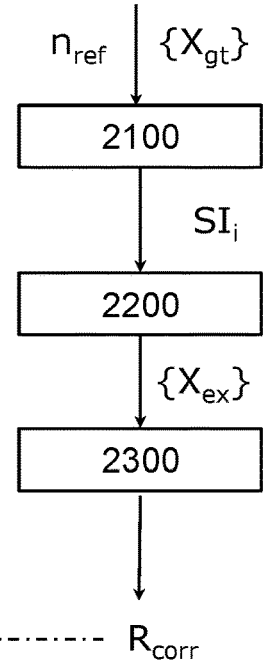
FIGS. 4B and 4C illustrate flow charts of methods for determining a correction function according to embodiments.

Optionally, any of the methods as described herein may use a stored correction function $R_{corr}$ taking into account corneal refraction to correct one or more parameters of the eye and/or the further eye of the subject. The correction function may be designed to take as input at least one parameter of one eye only, or may take as joint input parameters from several eyes. Applying the correction function $R_{corr}$ can be performed in a subsequent step 1600, 3600 at the end of any method as herein described, in particular the monocular and binocular methods previously described, indicated as method B in FIG. 4A. The basic principle of generating the correction function is the same in all cases and is illustrated in FIG. 4B as a flow chart of a method 2000.

In a first step 2100, synthetic camera images $SI_i$ of several model eyeballs of an eye H with varying effective corneal refraction index $n_{ref}$ and a plurality of given values $\{X_{gt}\}$ of one or more parameters $\{X\}$ of the model eyeball are determined using a model of the camera such as a pinhole model, assuming full perspective projection. For example, a ray tracer may be used to generate the synthetic camera images. For accuracy reasons, synthetic images may be ray traced at arbitrarily large image resolutions.

In step 2200, the synthetic camera images $SI_i$ are used to determine expected values of the one or more parameters $\{X_{ex}\}$. As explained below in more detail with regard to FIG. 4C, the expected values of the one or more parameters $\{X_{ex}\}$ are typically determined in analogy to any of the methods used to determine one or more parameters of an eye and/or a further eye of a subject as described herein, but based on the synthetic camera images $SI_i$.

Thereafter, the correction function $R_{corr}(\{X_{ex}\}, n_{ref}) = \{X_{gt}\}$ mapping, depending on the effective corneal refraction index $n_{ref}$, the expected values $\{X_{ex}\}$ to the respective given (ground truth) values $\{X_{gt}\}$ may be determined in a step 2300. $n_{ref}$ plays the role of an independent parameter to be able to account for variations in the effective refractive index of the cornea across subjects.

Generating said mapping is typically achieved by a (multivariate) polynomial regression analysis.

As indicated by the dashed-dotted arrow in FIGS. 4A and 4B the correction function $R_{corr}$ may be used to correct the parameters determined by method A or by method C.

The correction function $R_{corr}$ may be calculated as a single correction function in one stage only, such that $$R_{corr}(g_{ex}, r_{ex}, M_{ex}, n_{ref}) = (g_{gt}, r_{gt}, M_{gt}) \quad \text{(Eq.4)}$$

In (Eq. 4) subscripts 'gt' and 'ex' refer to the eyeball model parameters set for generating the synthetic camera images and the (expected) eyeball parameters determined from the synthetic camera images, respectively. Therein, the correction function may be designed such that it takes parameters from one eye only as input, or from more than one eye. For example. {g, r, M, $n_{ref}$} may stand for gaze direction, pupil radius, eyeball center and refraction index of one or of both eyes of a subject.

Note that due to the nonlinear nature of corneal refraction, the derivation of an exact closed-form representation of $R_{corr}$ is challenging. However, $R_{corr}$ may be estimated by an empirical correction function in the following manner.

After fixing $M_{gt}$ at a position randomly drawn from a range of practically relevant eyeball positions corresponding to a typical geometric setup of the eye camera, a number of synthetic eye images are generated for each fixed value of $n_{ref}$ randomly drawn from [1.1, 1.4], with gaze angles φ and θ (forming $g_{gt}$) randomly chosen from a uniform distribution between −50° and 50°, and with pupil radii $r_{gt}$ randomly chosen from a uniform distribution between 0.5 mm and 4.5 mm. Pupil contours are extracted from all images, based on which eyeball parameters are then determined as explained below with regard to FIG. 4C. Typically, a large number N of parameter tuples $\{g_{ex}, r_{ex}, M_{ex}, n_{ref}\}^i$, $\{g_{gt}, r_{gt}, M_{gt}\}^i$ with i=1 . . . N maybe determined this way and used to estimate $R_{corr}$ in a least-squares sense by means of a multivariate polynomial regression. For example, N maybe of the order of $10^3$ or even $10^6$ and the degree of the polynomial regression may for example be three, five or seven.

Figure 4C:
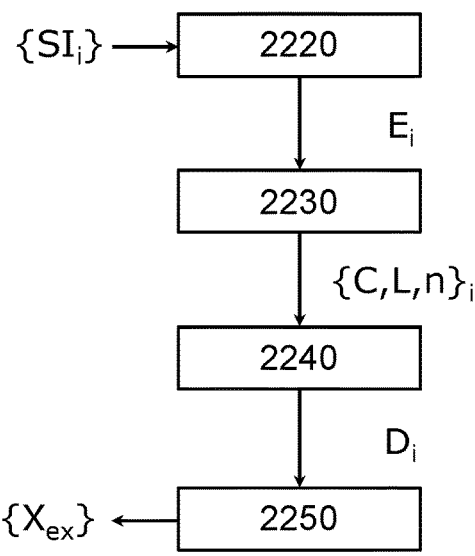

FIG. 4C illustrates a flow chart of step 2200 of the method 2000 explained above with regard to FIG. 4B.

In a first step 2220, in each synthetic camera image $SI_i$ a respective ellipse $E_i$ at least substantially representing a border of the pupil (of the model eye used for generating the synthetic camera images $SI_i$) is determined. The synthetic images may represent a monocular setup and thus comprise images of a single eye, or may represent a binocular setup and thus comprise images showing more than one eye or comprise pairs of images each showing a different eye of a synthetic user.

Thereafter, respective orientation vectors $n_i$ of circles $C_i$ and center lines $L_i$ on which a center of the respective circle $C_i$ is located are determined in step 2230 using the camera model used for generating the synthetic camera images $SI_i$, so that a projection of the circle $C_i$, in a direction parallel to the first center line $L_i$, onto the image plane of the camera model reproduces the respective ellipse $E_i$.

Thereafter, respective eye intersecting lines $D_i$ expected to intersect a center of the eyeball may be determined in step 2240 as lines which are, in the direction of the respective orientation vector $n_i$, parallel-shifted to the respective center line $L_i$ by the expected distance R between the center of the eyeball and the center of the pupil (of the model eye).

Thereafter, in step 2250 the eye intersecting lines $D_i$ may be used to determine the expected values of the pupil radii, gaze directions and eyeball centers (for example as least square intersecting point in a monocular setup or leveraging further constraints as explained previously in the context of binocular methods) as a parameters $X_{ex}$.

According to the present disclosure, methods for generating data suitable for determining parameters of an eye are provided, which open the way to a fast non-iterative approach to the tasks of (refraction-aware) 3D gaze prediction and pupillometry based on pupil contours alone. Leveraging geometrical insights with regard to the two-sphere eye model and/or with regard to human ocular physiology, these tasks are cast as a (least-squares) intersection of lines in a monocular, respectively an even simpler analytical geometry problem in a binocular setting. Systematic errors due to corneal refraction may be accounted for by means of empirical correction function(s).

Although various exemplary embodiments of the invention have been disclosed, it will be apparent to those skilled in the art that various changes and modifications can be made which will achieve some of the advantages of the invention without departing from the spirit and scope of the invention. The present invention is therefore limited only by the following claims and their legal equivalents.

REFERENCES

[1] L. Swirski and N. Dodgson: "A fully-automatic, temporal approach to single camera, glint-free 3D eye model fitting", Proc. PETMEI Lund/Sweden, 13 Aug. 2013
[2] R. Navarro, J. Santamaría, J. Bescós: "Accommodation-dependent model of the human eye with aspherics," J. Opt. Soc. Am. A 2(8), 1273-1281 (1985)

REFERENCE NUMBERS 1 head wearable device, head wearable spectacles device
2 main body, spectacles body
3 nose bridge portion
4 frame
5 illumination means
6
7 computing and control unit
8
9
10 left side
11 left ocular opening
12 left lateral portion
13 left holder/left temple (arm)
14 left camera
15 optical axis (left camera)
16
17 left inner eye camera placement zone
18 left outer eye camera placement zone
19 left eye
20 right side
21 right ocular opening
22 right lateral portion
23 right holder/right temple (arm)
24 right camera
25 optical axis (right camera)
26
27 right inner eye camera placement zone
28 left outer eye camera placement zone
29 right eye
30 bounding cuboid
31 left lateral surface
32 right lateral surface
33 upper surface
34 lower surface
100 middle plane
101 horizontal direction
102 vertical direction
103 down
104 up
105 front
106 back
$\alpha, \gamma$ angle of inner/outer left camera 14
$\beta, \delta$ angle of inner/outer right camera 24
$>=1000$ methods, method steps

The invention claimed is:

1. A method for generating data suitable for determining one or more parameters of at least one eye of a subject, the eye comprising an eyeball and an iris defining a pupil, the method comprising:
receiving image data of an eye at a first time from a camera of known camera intrinsics and defining an image plane;
determining a first ellipse in the image data, the first ellipse at least substantially representing a border of the pupil at the first time;
using the camera intrinsics and the first ellipse to determine, with respect to a 3D coordinate system, a 3D orientation vector of a first circle in 3D and a first center line on which a center of the first circle is located in 3D, so that a projection of the first circle, in a direction parallel to the first center line, onto the image plane is expected to reproduce the first ellipse; and
determining, with respect to the 3D coordinate system, a first eye intersecting line in 3D expected to intersect a 3D center of the eyeball at the first time as a line which is, in the direction of the orientation vector, parallel-shifted to the first center line by an expected distance between the center of the eyeball and a center of the pupil.

2. The method of claim 1, further comprising:
receiving image data of a further eye of the subject at a second time, substantially corresponding to the first time, from a camera of known camera intrinsics and defining an image plane, the further eye comprising a further eyeball and a further iris defining a further pupil;
determining a further ellipse in the image data, the further ellipse at least substantially representing the border of the further pupil of the further eye at the second time;
using the camera intrinsics and the further ellipse to determine a 3D orientation vector of a further circle in 3D and a further center line on which a center of the further circle is located in 3D, so that a projection of the further circle, in a direction parallel to the further center line, onto the image plane is expected to reproduce the further ellipse; and
determine a further eye intersecting line in 3D expected to intersect a 3D center of the further eyeball at the second time as a line which is, in the direction of the 3D orientation vector of the further circle, parallel-shifted to the further center line by an expected distance between the center of the further eyeball and a center of the further pupil.

3. The method of claim 2, further comprising using the first eye intersecting line and the further eye intersecting line to determine expected coordinates of the center of the eyeball and of the center of the further eyeball, such that each eyeball center lies on the respective eye intersecting line and the 3D distance between the eyeball centers corresponds to a predetermined value, in particular a predetermined inter-eyeball distance.

4. The method of claim 3, further comprising determining the expected coordinates of the center of the eyeball and of the center of the further eyeball, such that the radius of the first circle in 3D and the radius of the further circle in 3D are substantially equal, thereby also determining said radius.

5. The method of claim 3, wherein the predetermined distance value between the center of the eyeball and the center of the further eyeball is an average value, in particular a physiological constant or population average, or an individually estimated or measured value of the subject.

6. The method of claim 3, further comprising using the expected coordinates of the center of the eyeball and/or of the center of the further eyeball to determine for a later time, using later image data of the eye and/or the further eye acquired at the later time at least one of an expected optical axis, an expected orientation, an expected visual axis, and an expected size or radius of the pupil of the eye and/or the further eye.

7. The method of claim 2, wherein the image data of the eye and the further eye is produced using a single camera or using several cameras the relative poses of which are known.

8. The method of claim 1, wherein the center of the eyeball is assumed to have at least substantially non-varying co-ordinates in the co-ordinate system while the image date of the eye are acquired by the camera, wherein the respective 3D orientation vector points away from the camera, wherein the camera defines a 3D coordinate system, and/or wherein at least the respective orientation vectors, center lines and eye intersecting lines are determined with respect to the 3D coordinate system of the respective camera, and/or transformed into a common 3D coordinate system via the known relative camera poses.

9. The method of claim 1, wherein the expected distance between the center of the eyeball and the center of the pupil is an average value, in particular a physiological constant or population average.

10. The method of claim 1, further comprising at least one of:
   determining for at least one time an expected 3D gaze direction of the eye and/or the further eye as a vector which is antiparallel to the respective 3D orientation vector; and
   using a stored correction function taking into account corneal refraction to correct the parameter of the eye and/or the further eye of the subject and/or to determine a corrected value for at least one of the center of the eyeball, the expected gaze direction, the expected optical axis, the expected orientation, the expected visual axis, and the expected size or radius of the pupil of the eye and/or the further eye of the subject.

11. The method claim 10, wherein determining the stored correction function for at least one parameter of at least one eye comprises:
   calculating, using the known camera intrinsics, synthetic camera images of several model eyeballs of at least one eye with varying effective corneal refraction index, for a plurality of given values of the at least one parameter of the model eyeballs;
   using the synthetic camera images to determine expected values of the at least one parameter; and
   using the expected values of the at least one parameter and the given values of the at least one parameter to determine the correction function, which maps, depending on the effective corneal refraction index, the expected values of the at least one parameter to the respective given values of the at least one parameter.

12. The method of claim 11, wherein the given values comprise at least one of given coordinates of respective centers of the model eyeballs, given radii of a pupil of the model eyeballs, and given gaze directions of the model eyeballs, wherein determining the expected values comprises applying the method of claim 1 to the synthetic camera images, wherein determining the correction function comprises a multivariate polynomial regression analysis, and/or wherein calculating the synthetic camera images comprises raytracing an arrangement of a camera model describing the camera and the model eyeballs arranged in the field of view of the camera model, and/or wherein two-sphere eye models are used as model of the eye.

13. The method of claim 1, wherein the respective center line and/or the respective eye intersecting line is determined using a model of the camera and/or a three-dimensional eye model, wherein the three-dimensional eye model is a two-sphere eye model, wherein the camera is modelled as a pinhole camera, wherein the model of the camera comprises at least one of a focal length, a shift of a central image pixel, a shear parameter, and a distortion parameter, wherein the method does not take into account a glint from the eye for generating data suitable for determining the parameter of the eye, and/or wherein the method is glint-free, and/or wherein the method does not use structured light and/or special purpose illumination to derive parameters of the eye.

14. A system, comprising:
   a device comprising at least one camera of known camera intrinsics for producing image data referring to at least one eye of a subject, the at least one camera comprising a sensor defining an image plane, the at least one eye comprising an eyeball and an iris defining a pupil; and
   a computing and control unit configured to:
      receive image data of the at least one eye at a first time from the at least one camera;
      determine a first ellipse in the image data, the first ellipse at least substantially representing a border of the pupil at the first time;
      use the camera intrinsics and the first ellipse to determine, with respect to a 3D coordinate system, a 3D orientation vector of a first circle in 3D and a first center line on which a center of the first circle is located in 3D, so that a projection of the first circle, in a direction parallel to the first center line, onto the image plane is expected to reproduce the first ellipse; and
      determine, with respect to the 3D coordinate system, a first eye intersecting line in 3D expected to intersect a 3D center of the eyeball at the first time as a line which is, in the direction of the orientation vector, parallel-shifted to the first center line by an expected distance between the center of the eyeball and a center of the pupil.

15. The system of claim 14, wherein the computing and control unit is configured to:
   receive image data of a further eye of the subject at a second time, substantially corresponding to the first time, from a camera of known camera intrinsics and defining an image plane, the further eye comprising a further eyeball and a further iris defining a further pupil;
   determine a further ellipse in the image data, the further ellipse at least substantially representing the border of the further pupil of the further eye at the second time;
   use the camera intrinsics and the further ellipse to determine a 3D orientation vector of a further circle in 3D and a further center line on which a center of the further circle is located in 3D, so that a projection of the further circle, in a direction parallel to the further center line, onto the image plane is expected to reproduce the further ellipse;

determine a further eye intersecting line in 3D expected to intersect a 3D center of the further eyeball at the second time as a line which is, in the direction of the 3D orientation vector of the further circle, parallel-shifted to the further center line by an expected distance between the center of the further eyeball and a center of the further pupil; and use the first eye intersecting line and the further eye intersecting line to determine expected coordinates of the center of the eyeball and of the center of the further eyeball, such that each eyeball center lies on the respective eye intersecting line and the 3D distance between the eyeball centers corresponds to a predetermined value, in particular a predetermined inter-eyeball distance; and wherein the computing and control unit is configured to receive the image data of the eye and the image data of the further eye from a single camera or from different cameras the relative poses of which are known, and is further configured to determine at least the respective orientation vectors, center lines and eye intersecting lines with respect to the 3D coordinate system of the respective camera, and/or transform them into a common 3D coordinate system via the known relative camera poses.

16. The system of claim 14, wherein the expected distance between the center of the further eyeball and the center of the further pupil is at least substantially equal to the expected distance between the center of the eyeball and the center of the pupil, and wherein the expected distance is an average value, in particular a physiological constant or population average.

17. The system of claim 14, wherein the computing and control unit is configured to use a stored correction function taking into account corneal refraction to determine a corrected value for the at least one parameter of at least one eye of a subject, in particular for at least one of the center of the eyeball, the expected gaze direction of the eye, the expected optical axis of the eye, the expected orientation of the eye, the expected visual axis of the eye, and the expected size or radius of the pupil.

18. The system of claim 14, wherein a position and/or orientation of the respective camera or cameras is/are non-adjustably fixed or adjustable and/or fixable with respect to a frame of the device, in particular such that the relative poses of the cameras are known per construction or can be measured after having been adjusted.

19. The system of claim 14, wherein the device is a head-wearable device or a remote eye-tracking device, and/or wherein the computing and control unit is at least partly integrated into the device and/or at least partly provided by a companion device of the system, in particular a mobile companion device.

20. A non-transitory computer-readable storage medium comprising instructions which, when executed by a one or more processors of a system cause the system to carry out the steps of:

receiving image data of an eye at a first time from a camera of known camera intrinsics and defining an image plane;

determining a first ellipse in the image data, the first ellipse at least substantially representing a border of the pupil at the first time;

using the camera intrinsics and the first ellipse to determine, with respect to a 3D coordinate system, a 3D orientation vector of a first circle in 3D and a first center line on which a center of the first circle is located in 3D, so that a projection of the first circle, in a direction parallel to the first center line, onto the image plane is expected to reproduce the first ellipse; and determining, with respect to the 3D coordinate system, a first eye intersecting line in 3D expected to intersect a 3D center of the eyeball at the first time as a line which is, in the direction of the orientation vector, parallel-shifted to the first center line by an expected distance between the center of the eyeball and a center of the pupil.

* * * * *